(12) United States Patent
Gharib et al.

(10) Patent No.: US 10,016,263 B2
(45) Date of Patent: *Jul. 10, 2018

(54) APPARATUS AND METHODS FOR TREATING ROOT CANALS OF TEETH

(71) Applicant: SONENDO, INC., Laguna Hills, CA (US)

(72) Inventors: Morteza Gharib, San Marino, CA (US); Joshua Adams, Pasadena, CA (US); Erik Hars, Mission Viejo, CA (US); Bjarne Bergheim, Mission Viejo, CA (US); Karl Stocks, Oceanside, CA (US); Lance Doherty, Cerritos, CA (US)

(73) Assignee: SONENDO, INC., Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/217,843

(22) Filed: Jul. 22, 2016

(65) Prior Publication Data

US 2016/0324600 A1    Nov. 10, 2016

Related U.S. Application Data

(63) Continuation of application No. 14/628,500, filed on Feb. 23, 2015, which is a continuation of application
(Continued)

(51) Int. Cl.
*A61C 17/02* (2006.01)
*A61C 17/16* (2006.01)
(Continued)

(52) U.S. Cl.
CPC ............... *A61C 17/02* (2013.01); *A61C 5/40* (2017.02); *A61C 5/50* (2017.02); *A61C 17/0202* (2013.01); *A61C 17/16* (2013.01)

(58) Field of Classification Search
CPC ........ A61C 5/02; A61C 17/0202; A61C 17/07
See application file for complete search history.

(56) References Cited

U.S. PATENT DOCUMENTS

| 1,500,107 A | 7/1924 | Chandler |
| 2,108,558 A | 2/1938 | Jackman |

(Continued)

FOREIGN PATENT DOCUMENTS

| AU | 2012-202315 A1 | 4/2012 |
| AU | 2007140780 | 5/2014 |

(Continued)

OTHER PUBLICATIONS

U.S. Appl. No. 61/701,947, filed Sep. 17, 2012, Laufer.
(Continued)

*Primary Examiner* — Ralph Lewis
(74) *Attorney, Agent, or Firm* — Knobbe Matens Olson & Bear, LLP

(57) ABSTRACT

Apparatus and methods for endodontic treatment of teeth provide effective cleaning of organic material (such as pulp and diseased tissue) from the root canal system. In an embodiment, a compressor system generates high pressure liquid (e.g., water) that flows through an orifice to produce a high-velocity collimated jet of liquid. The high-velocity jet is directed toward a surface of a tooth, for example, an exposed dentinal surface, and impingement of the jet onto the surface generates an acoustic wave that propagates throughout the tooth. The acoustic wave effectively detaches organic material from dentinal surfaces and tubules. The detached organic material is flushed from the root canal system by the liquid jet and/or by additional irrigation.

20 Claims, 16 Drawing Sheets

US 10,016,263 B2

Page 2

Related U.S. Application Data

No. 14/304,737, filed on Jun. 13, 2014, which is a continuation of application No. 11/737,710, filed on Apr. 19, 2007, now Pat. No. 8,753,121.

(60) Provisional application No. 60/793,452, filed on Apr. 20, 2006.

(51) Int. Cl.
  *A61C 5/40* (2017.01)
  *A61C 5/50* (2017.01)

(56) References Cited

U.S. PATENT DOCUMENTS

| | | |
|---|---|---|
| 3,023,306 A | 2/1962 | Kester |
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,624,907 A | 12/1971 | Brass et al. |
| 3,703,170 A | 11/1972 | Ryckman, Jr. |
| 3,756,225 A | 9/1973 | Moret et al. |
| 3,828,770 A | 8/1974 | Kuris et al. |
| 3,921,296 A | 11/1975 | Harris |
| 3,930,505 A | 1/1976 | Wallach |
| 3,962,790 A | 6/1976 | Riitano et al. |
| 4,021,921 A | 5/1977 | Detaille |
| 4,060,600 A | 11/1977 | Vit |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,376,835 A | 3/1983 | Schmitt et al. |
| 4,386,911 A | 6/1983 | Maloney et al. |
| 4,424,036 A | 1/1984 | Lokken |
| 4,474,251 A | 2/1984 | Johnson, Jr. |
| 4,492,575 A | 1/1985 | Mabille |
| 4,534,542 A | 8/1985 | Russo |
| 4,539,987 A | 9/1985 | Nath et al. |
| 4,608,017 A | 8/1986 | Sadohara |
| 4,659,218 A | 4/1987 | de Lasa et al. |
| 4,661,070 A | 4/1987 | Friedman |
| 4,676,586 A | 6/1987 | Jones et al. |
| 4,676,749 A | 6/1987 | Mabille |
| 4,684,781 A | 8/1987 | Frish et al. |
| 4,789,335 A | 12/1988 | Geller et al. |
| 4,872,837 A | 10/1989 | Issalene et al. |
| 4,941,459 A | 7/1990 | Mathur |
| 4,957,436 A | 9/1990 | Ryder |
| 4,973,246 A | 11/1990 | Black et al. |
| 4,985,027 A | 1/1991 | Dressel |
| 4,993,947 A | 2/1991 | Grosrey |
| 5,013,300 A | 5/1991 | Williams |
| 5,029,576 A | 7/1991 | Evans, Sr. |
| 5,037,431 A | 8/1991 | Summers et al. |
| 5,046,950 A | 9/1991 | Favonio |
| 5,055,048 A | 10/1991 | Vassiliadis et al. |
| 5,066,232 A | 11/1991 | Negri et al. |
| 5,094,256 A | 3/1992 | Barth |
| 5,112,224 A | 5/1992 | Shirota |
| 5,116,227 A | 5/1992 | Levy |
| 5,173,049 A | 12/1992 | Levy |
| 5,173,050 A | 12/1992 | Dillon |
| 5,188,532 A | 2/1993 | Levy |
| 5,188,634 A | 2/1993 | Hussein et al. |
| 5,194,723 A | 3/1993 | Cates et al. |
| 5,195,952 A | 3/1993 | Solnit et al. |
| 5,224,942 A | 7/1993 | Beuchat et al. |
| 5,267,856 A | 12/1993 | Wolbarsht et al. |
| 5,267,995 A | 12/1993 | Doiron et al. |
| 5,269,777 A | 12/1993 | Doiron et al. |
| 5,292,253 A | 3/1994 | Levy |
| 5,295,828 A | 3/1994 | Grosrey |
| 5,307,839 A | 5/1994 | Loebker et al. |
| 5,322,504 A | 6/1994 | Doherty et al. |
| 5,324,200 A | 6/1994 | Vassiliadis et al. |
| 5,326,263 A | 7/1994 | Weissman |
| 5,334,019 A | 8/1994 | Goldsmith et al. |
| 5,380,201 A | 1/1995 | Kawata |
| 5,387,376 A | 2/1995 | Gasser |
| D356,866 S | 3/1995 | Meller |
| 5,399,089 A | 3/1995 | Eichman et al. |
| 5,428,699 A | 6/1995 | Pond |
| 5,435,724 A | 7/1995 | Goodman et al. |
| 5,474,451 A | 12/1995 | Dalrymple et al. |
| 5,490,779 A | 2/1996 | Malmin |
| 5,503,559 A | 4/1996 | Vari |
| 5,540,587 A | 7/1996 | Malmin |
| 5,547,376 A | 8/1996 | Harrel |
| 5,554,896 A | 9/1996 | Hogan |
| 5,562,692 A | 10/1996 | Bair |
| 5,564,929 A | 10/1996 | Alpert |
| 5,570,182 A | 10/1996 | Nathel et al. |
| 5,591,184 A | 1/1997 | McDonnell et al. |
| 5,601,430 A | 2/1997 | Kutsch et al. |
| 5,620,414 A | 4/1997 | Campbell, Jr. |
| 5,639,239 A | 6/1997 | Earle |
| 5,642,997 A | 7/1997 | Gregg et al. |
| 5,643,299 A | 7/1997 | Bair |
| 5,660,817 A | 8/1997 | Masterman et al. |
| 5,662,501 A | 9/1997 | Levy |
| 5,674,226 A | 10/1997 | Doherty et al. |
| 5,688,486 A | 11/1997 | Watson et al. |
| 5,720,894 A | 2/1998 | Neev et al. |
| 5,730,727 A | 3/1998 | Russo |
| 5,735,815 A | 4/1998 | Bair |
| 5,740,291 A | 4/1998 | De Lasa et al. |
| 5,755,752 A | 5/1998 | Segal |
| 5,759,159 A | 6/1998 | Masreliez |
| 5,762,501 A | 6/1998 | Levy |
| 5,795,153 A | 8/1998 | Rechmann |
| 5,797,745 A | 8/1998 | Ruddle |
| 5,810,037 A | 9/1998 | Sasaki et al. |
| 5,816,807 A | 10/1998 | Matsutani et al. |
| 5,820,373 A | 10/1998 | Okano et al. |
| 5,825,958 A | 10/1998 | Gollihar et al. |
| 5,839,896 A | 11/1998 | Hickok et al. |
| 5,842,863 A | 12/1998 | Bruns et al. |
| 5,846,080 A | 12/1998 | Schneider |
| 5,853,384 A | 12/1998 | Bair |
| 5,865,790 A | 2/1999 | Bair |
| 5,868,570 A | 2/1999 | Hickok et al. |
| 5,874,677 A | 2/1999 | Bab et al. |
| 5,879,160 A | 3/1999 | Ruddle |
| 5,897,314 A | 4/1999 | Hack et al. |
| 5,915,965 A | 6/1999 | Ohlsson et al. |
| 5,921,775 A | 7/1999 | Buchanan |
| 5,968,039 A | 10/1999 | Deutsch |
| 5,975,897 A | 11/1999 | Propp et al. |
| 5,989,023 A | 11/1999 | Summer et al. |
| 6,004,319 A | 12/1999 | Goble et al. |
| 6,019,605 A | 2/2000 | Myers |
| 6,053,735 A | 4/2000 | Buchanan |
| 6,079,979 A | 6/2000 | Riitano |
| 6,122,300 A | 9/2000 | Frieberg et al. |
| 6,129,721 A | 10/2000 | Kataoka et al. |
| 6,139,319 A | 10/2000 | Sauer et al. |
| 6,143,011 A | 11/2000 | Hood et al. |
| 6,159,006 A | 12/2000 | Cook et al. |
| 6,162,052 A | 12/2000 | Kokubu |
| 6,162,177 A | 12/2000 | Bab et al. |
| 6,162,202 A | 12/2000 | Sicurelli et al. |
| 6,164,966 A | 12/2000 | Turdiu et al. |
| 6,179,617 B1 | 1/2001 | Ruddle |
| 6,190,318 B1 | 2/2001 | Bab et al. |
| 6,221,031 B1 | 4/2001 | Heraud |
| 6,224,378 B1 * | 5/2001 | Valdes .......... A61C 1/0084 433/224 |
| 6,227,855 B1 | 5/2001 | Hickok et al. |

(56) References Cited

U.S. PATENT DOCUMENTS

| | | |
|---|---|---|
| 6,245,032 B1 | 6/2001 | Sauer et al. |
| 6,282,013 B1 | 8/2001 | Ostler et al. |
| 6,288,499 B1 | 9/2001 | Rizoiu et al. |
| 6,290,502 B1 | 9/2001 | Hugo |
| 6,312,440 B1 | 11/2001 | Hood et al. |
| 6,315,557 B1 | 11/2001 | Messick |
| 6,343,929 B1 | 2/2002 | Fischer |
| 6,386,871 B1 | 5/2002 | Rossell |
| 6,390,815 B1 | 5/2002 | Pond |
| 6,428,319 B1 | 8/2002 | Lopez et al. |
| 6,440,103 B1 | 8/2002 | Hood et al. |
| 6,454,566 B1 | 9/2002 | Lynch et al. |
| 6,464,498 B1 | 10/2002 | Pond |
| 6,485,304 B2 | 11/2002 | Beerstecher et al. |
| 6,497,572 B2 * | 12/2002 | Hood ............. A61C 1/0084 433/81 |
| 6,511,493 B1 | 1/2003 | Moutafis et al. |
| 6,514,077 B1 | 2/2003 | Wilk |
| 6,527,766 B1 | 3/2003 | Bair |
| 6,538,739 B1 | 3/2003 | Visuri et al. |
| 6,562,050 B1 | 5/2003 | Owen |
| 6,572,709 B1 | 6/2003 | Kaneda et al. |
| 6,602,074 B1 | 8/2003 | Suh et al. |
| 6,616,447 B1 | 9/2003 | Rizoiu et al. |
| 6,638,219 B1 | 10/2003 | Asch et al. |
| 6,641,394 B2 | 11/2003 | Garman |
| 6,663,386 B1 | 12/2003 | Moelsgaard |
| 6,676,409 B2 | 1/2004 | Grant |
| 6,783,364 B1 | 8/2004 | Juan |
| 6,817,862 B2 | 11/2004 | Hickok |
| 6,821,272 B2 | 11/2004 | Rizoiu et al. |
| D499,486 S | 12/2004 | Kuhn et al. |
| 6,827,766 B2 | 12/2004 | Carnes et al. |
| 6,881,061 B2 | 4/2005 | Fisher |
| 6,910,887 B2 | 6/2005 | Van Den Houdt |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,011,521 B2 | 3/2006 | Sierro et al. |
| 7,011,644 B1 | 3/2006 | Andrew et al. |
| 7,014,465 B1 | 3/2006 | Marais |
| 7,044,737 B2 | 5/2006 | Fu |
| 7,090,497 B1 | 8/2006 | Harris |
| 7,108,693 B2 | 9/2006 | Rizoiu et al. |
| 7,115,100 B2 | 10/2006 | McRury et al. |
| 7,147,468 B2 | 12/2006 | Snyder et al. |
| 7,163,400 B2 | 1/2007 | Cozean et al. |
| 7,238,342 B2 | 7/2007 | Torabinejad et al. |
| 7,261,561 B2 | 8/2007 | Ruddle et al. |
| 7,269,306 B1 | 9/2007 | Koeneman et al. |
| 7,270,544 B2 | 9/2007 | Schemmer et al. |
| 7,288,086 B1 | 10/2007 | Andriasyan |
| 7,296,318 B2 | 11/2007 | Mourad et al. |
| 7,306,459 B1 | 12/2007 | Williams et al. |
| 7,306,577 B2 | 12/2007 | Lemoine et al. |
| 7,326,054 B2 | 2/2008 | Todd et al. |
| 7,356,225 B2 | 4/2008 | Loebel |
| 7,384,419 B2 | 6/2008 | Jones et al. |
| 7,415,050 B2 | 8/2008 | Rizoiu et al. |
| 7,421,186 B2 | 9/2008 | Boutoussov et al. |
| 7,445,618 B2 | 11/2008 | Eggers et al. |
| 7,470,124 B2 | 12/2008 | Bornstein |
| 7,485,116 B2 | 2/2009 | Cao |
| 7,549,861 B2 | 6/2009 | Ruddle et al. |
| 7,620,290 B2 | 11/2009 | Rizoiu et al. |
| 7,630,420 B2 | 12/2009 | Boutoussov |
| 7,641,668 B2 | 1/2010 | Perry et al. |
| 7,670,141 B2 | 3/2010 | Thomas et al. |
| 7,695,469 B2 | 4/2010 | Boutoussov et al. |
| 7,696,466 B2 | 4/2010 | Rizoiu et al. |
| 7,702,196 B2 | 4/2010 | Boutoussov et al. |
| 7,748,979 B2 | 7/2010 | Nahlieli |
| 7,778,306 B2 | 8/2010 | Marincek et al. |
| 7,815,630 B2 | 10/2010 | Rizoiu et al. |
| 7,817,687 B2 | 10/2010 | Rizoiu et al. |
| 7,833,016 B2 | 11/2010 | Gharib et al. |
| 7,845,944 B2 | 12/2010 | DiGasbarro |
| 7,867,224 B2 | 1/2011 | Lukac et al. |
| 7,901,373 B2 | 3/2011 | Tavger |
| 7,909,817 B2 | 3/2011 | Griffin et al. |
| 7,916,282 B2 | 3/2011 | Duineveld et al. |
| 7,959,441 B2 | 6/2011 | Glover et al. |
| 7,970,027 B2 | 6/2011 | Rizoiu et al. |
| 7,970,030 B2 | 6/2011 | Rizoiu et al. |
| 7,980,854 B2 | 7/2011 | Glover et al. |
| 7,980,923 B2 | 7/2011 | Olmo et al. |
| 8,002,544 B2 | 8/2011 | Rizoiu et al. |
| 8,011,923 B2 | 9/2011 | Lukac et al. |
| 8,033,825 B2 | 10/2011 | Rizoiu et al. |
| 8,037,566 B2 | 10/2011 | Grez |
| 8,047,841 B2 | 11/2011 | Jefferies |
| 8,128,401 B2 | 3/2012 | Ruddle et al. |
| 8,152,797 B2 | 4/2012 | Boutoussov et al. |
| 8,204,612 B2 | 6/2012 | Feine et al. |
| 8,235,719 B2 | 8/2012 | Ruddle et al. |
| 8,295,025 B2 | 10/2012 | Edel et al. |
| 8,298,215 B2 | 10/2012 | Zinn |
| 8,317,514 B2 | 11/2012 | Weill |
| 8,322,910 B2 | 12/2012 | Gansmuller et al. |
| 8,328,552 B2 | 12/2012 | Ruddle |
| 8,388,345 B2 | 3/2013 | Ruddle |
| 8,419,719 B2 | 4/2013 | Rizoiu et al. |
| 8,439,676 B2 | 5/2013 | Florman |
| 8,506,293 B2 | 8/2013 | Pond |
| 8,617,090 B2 | 12/2013 | Fougere et al. |
| D699,180 S | 2/2014 | Sweere et al. |
| 8,672,678 B2 | 3/2014 | Gramann et al. |
| 8,684,956 B2 | 4/2014 | McDonough et al. |
| 8,709,057 B2 | 4/2014 | Tettamanti et al. |
| 8,740,957 B2 | 6/2014 | Masotti |
| 8,747,005 B2 | 6/2014 | Kemp et al. |
| 8,753,121 B2 * | 6/2014 | Gharib ............... A61C 5/02 433/224 |
| 8,758,010 B2 | 6/2014 | Yamanaka et al. |
| 8,801,316 B1 | 8/2014 | Abedini |
| 8,834,457 B2 | 9/2014 | Cao |
| 8,977,085 B2 | 3/2015 | Walsh et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,025,625 B2 | 5/2015 | Skrabelj et al. |
| 9,050,157 B2 | 6/2015 | Boyd et al. |
| 9,084,651 B2 | 7/2015 | Laufer |
| 9,101,377 B2 | 8/2015 | Boutoussov et al. |
| 9,186,222 B2 | 11/2015 | Marincek et al. |
| D745,966 S | 12/2015 | Piorek et al. |
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 9,492,244 B2 | 11/2016 | Bergheim et al. |
| 9,504,536 B2 | 11/2016 | Bergheim et al. |
| 9,572,632 B2 | 2/2017 | Lukac et al. |
| 9,579,174 B2 | 2/2017 | Yamamoto et al. |
| 9,610,125 B2 | 4/2017 | Kazic et al. |
| 2001/0041324 A1 | 11/2001 | Riitano |
| 2002/0012897 A1 | 1/2002 | Tingley et al. |
| 2002/0072032 A1 | 6/2002 | Senn et al. |
| 2002/0090594 A1 | 7/2002 | Riitano et al. |
| 2002/0108614 A1 | 8/2002 | Schultz |
| 2002/0183728 A1 | 12/2002 | Rosenberg et al. |
| 2003/0013064 A1 | 1/2003 | Zirkel |
| 2003/0096213 A1 | 5/2003 | Hickok et al. |
| 2003/0121532 A1 | 7/2003 | Coughlin et al. |
| 2003/0191429 A1 | 10/2003 | Andrew et al. |
| 2003/0207231 A1 | 11/2003 | Nance |
| 2003/0207232 A1 | 11/2003 | Todd et al. |
| 2003/0236517 A1 | 12/2003 | Appling |
| 2004/0038170 A1 | 2/2004 | Hiszowicz et al. |
| 2004/0048226 A1 | 3/2004 | Garman |
| 2004/0063074 A1 | 4/2004 | Fisher |
| 2004/0072122 A1 | 4/2004 | Hegemann |

(56) References Cited

U.S. PATENT DOCUMENTS

| | | |
|---|---|---|
| 2004/0073374 A1 | 4/2004 | Lockhart et al. |
| 2004/0101809 A1 | 5/2004 | Weiss et al. |
| 2004/0126732 A1 | 7/2004 | Nusstein |
| 2004/0127892 A1 | 7/2004 | Harris |
| 2004/0193236 A1 | 9/2004 | Altshuler |
| 2004/0210276 A1 | 10/2004 | Altshuler et al. |
| 2004/0224288 A1 | 11/2004 | Bornstein |
| 2005/0064371 A1 | 3/2005 | Soukos et al. |
| 2005/0096529 A1 | 5/2005 | Cooper et al. |
| 2005/0136375 A1 | 6/2005 | Sicurelli, Jr. et al. |
| 2005/0155622 A1 | 7/2005 | Leis |
| 2005/0170312 A1 | 8/2005 | Pond |
| 2005/0199261 A1 | 9/2005 | Vanhauwemeiren et al. |
| 2005/0277898 A1 | 12/2005 | Dimalanta et al. |
| 2005/0281530 A1 | 12/2005 | Rizoiu et al. |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0184071 A1 | 8/2006 | Klopotek |
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0240386 A1 | 10/2006 | Yaniv et al. |
| 2006/0246395 A1 | 11/2006 | Pond |
| 2006/0257819 A1 | 11/2006 | Johnson |
| 2006/0264808 A1 | 11/2006 | Staid et al. |
| 2007/0009449 A1 | 1/2007 | Kanca |
| 2007/0016177 A1 | 1/2007 | Vaynberg et al. |
| 2007/0016178 A1 | 1/2007 | Vaynberg et al. |
| 2007/0020576 A1 | 1/2007 | Osborn et al. |
| 2007/0042316 A1 | 2/2007 | Pichat et al. |
| 2007/0049911 A1 | 3/2007 | Brown |
| 2007/0072153 A1 | 3/2007 | Gross et al. |
| 2007/0083120 A1 | 4/2007 | Cain et al. |
| 2007/0148615 A1 | 6/2007 | Pond |
| 2007/0175502 A1 | 8/2007 | Sliwa |
| 2007/0179486 A1 | 8/2007 | Welch et al. |
| 2007/0265605 A1 | 11/2007 | Vaynberg et al. |
| 2007/0287125 A1 | 12/2007 | Weill |
| 2008/0014545 A1 | 1/2008 | Schippers |
| 2008/0032259 A1 | 2/2008 | Schoeffel |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0138772 A1 | 6/2008 | Bornstein |
| 2008/0155770 A1 | 7/2008 | Grez |
| 2008/0159345 A1 | 7/2008 | Bornstein |
| 2008/0160479 A1 | 7/2008 | Ruddle et al. |
| 2008/0160480 A1 | 7/2008 | Ruddle et al. |
| 2008/0188848 A1 | 8/2008 | Deutmeyer et al. |
| 2008/0199831 A1 | 8/2008 | Teichert et al. |
| 2008/0255498 A1 | 10/2008 | Houle |
| 2008/0285600 A1 | 11/2008 | Marincek et al. |
| 2009/0004621 A1 | 1/2009 | Quan et al. |
| 2009/0011380 A1 | 1/2009 | Wang |
| 2009/0042171 A1 | 2/2009 | Rizoiu et al. |
| 2009/0047624 A1 | 2/2009 | Tsai |
| 2009/0047634 A1 | 2/2009 | Calvert |
| 2009/0054881 A1 | 2/2009 | Krespi |
| 2009/0059994 A1 | 3/2009 | Nemes et al. |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0208898 A1 | 8/2009 | Kaplan |
| 2009/0211042 A1 | 8/2009 | Bock |
| 2009/0220908 A1 | 9/2009 | Divito et al. |
| 2009/0227185 A1 | 9/2009 | Summers et al. |
| 2009/0263759 A1 | 10/2009 | Van Herpern |
| 2010/0047734 A1 | 2/2010 | Harris et al. |
| 2010/0143861 A1 | 6/2010 | Gharib |
| 2010/0152634 A1 | 6/2010 | Dove |
| 2010/0160838 A1 | 6/2010 | Krespi |
| 2010/0229316 A1 | 9/2010 | Hohlbein et al. |
| 2010/0273125 A1 | 10/2010 | Janssen et al. |
| 2010/0330539 A1 | 12/2010 | Glover et al. |
| 2011/0027746 A1 | 2/2011 | McDonough et al. |
| 2011/0027747 A1 | 2/2011 | Fougere et al. |
| 2011/0072605 A1 | 3/2011 | Steur |
| 2011/0087605 A1 | 4/2011 | Pond |
| 2011/0111365 A1 | 5/2011 | Gharib et al. |
| 2011/0117517 A1 | 5/2011 | Bergheim et al. |
| 2011/0143310 A1 | 6/2011 | Hunter |
| 2011/0229845 A1 | 9/2011 | Chen |
| 2011/0256503 A1 | 10/2011 | Fraser |
| 2011/0269099 A1 | 11/2011 | Glover et al. |
| 2011/0270241 A1 | 11/2011 | Boutoussov |
| 2012/0135373 A1 | 5/2012 | Cheng et al. |
| 2012/0141953 A1 | 6/2012 | Mueller |
| 2012/0237893 A1 | 9/2012 | Bergheim |
| 2012/0276497 A1 | 11/2012 | Gharib |
| 2012/0282570 A1 | 11/2012 | Mueller |
| 2012/0321375 A1 | 12/2012 | Binner et al. |
| 2013/0040267 A1 | 2/2013 | Bergheim |
| 2013/0084544 A1 | 4/2013 | Boutoussov et al. |
| 2013/0084545 A1 | 4/2013 | Netchitailo et al. |
| 2013/0085486 A1 | 4/2013 | Boutoussov et al. |
| 2013/0131656 A1 | 5/2013 | Marincek et al. |
| 2013/0143180 A1 | 6/2013 | Glover et al. |
| 2013/0177865 A1 | 7/2013 | Ostler |
| 2013/0190738 A1 | 7/2013 | Lukac et al. |
| 2013/0216980 A1 | 8/2013 | Boronkay et al. |
| 2013/0236857 A1 | 9/2013 | Boutoussov et al. |
| 2013/0288195 A1 | 10/2013 | Mueller |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0072931 A1 | 3/2014 | Fougere et al. |
| 2014/0080090 A1 | 3/2014 | Laufer |
| 2014/0087333 A1 | 3/2014 | DiVito et al. |
| 2014/0099597 A1 | 4/2014 | Bergheim |
| 2014/0113243 A1 | 4/2014 | Boutoussov et al. |
| 2014/0124969 A1 | 5/2014 | Blaisdell et al. |
| 2014/0127641 A1 | 5/2014 | Hilscher et al. |
| 2014/0170588 A1 | 6/2014 | Miller et al. |
| 2014/0205965 A1 | 7/2014 | Boutoussov et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0261534 A1 | 9/2014 | Schepis |
| 2014/0272782 A1 | 9/2014 | Luettgen et al. |
| 2014/0349246 A1 | 11/2014 | Johnson et al. |
| 2015/0010878 A1 | 1/2015 | Seibel et al. |
| 2015/0010882 A1 | 1/2015 | Bergheim |
| 2015/0017599 A1 | 1/2015 | Marincek et al. |
| 2015/0044631 A1 | 2/2015 | Lifshitz et al. |
| 2015/0044632 A1 | 2/2015 | Bergheim et al. |
| 2015/0056567 A1 | 2/2015 | Fregoso et al. |
| 2015/0056570 A1 | 2/2015 | Kansal |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1 | 5/2015 | Breysse |
| 2015/0147717 A1 | 5/2015 | Taylor et al. |
| 2015/0147718 A1 | 5/2015 | Khakpour |
| 2015/0150650 A1 | 6/2015 | Netchitailo et al. |
| 2015/0173850 A1 | 6/2015 | Garrigues et al. |
| 2015/0173852 A1 | 6/2015 | Khakpour |
| 2015/0190597 A1 | 7/2015 | Zachar et al. |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0366634 A1 | 12/2015 | Gharib |
| 2015/0367142 A1 | 12/2015 | Kazic et al. |
| 2015/0374471 A1 | 12/2015 | Stangel et al. |
| 2016/0022392 A1 | 1/2016 | Chang et al. |
| 2016/0095679 A1 | 4/2016 | Khakpour |

(56) References Cited

U.S. PATENT DOCUMENTS

| | | |
|---|---|---|
| 2016/0100921 A1 | 4/2016 | Ungar |
| 2016/0113733 A1 | 4/2016 | Pond et al. |
| 2016/0128815 A1 | 5/2016 | Birdee et al. |
| 2016/0135581 A1 | 5/2016 | Pai |
| 2016/0149370 A1 | 5/2016 | Marincek et al. |
| 2016/0149372 A1 | 5/2016 | Marincek et al. |
| 2016/0367346 A1 | 12/2016 | Gharib |
| 2017/0027646 A1 | 2/2017 | DivVito et al. |
| 2017/0036253 A1 | 2/2017 | Lukac et al. |
| 2017/0056143 A1 | 3/2017 | Hyun |

FOREIGN PATENT DOCUMENTS

| | | |
|---|---|---|
| AU | 2011316839 | 8/2015 |
| AU | 2010319321 B2 | 4/2016 |
| CA | 2361482 | 6/2002 |
| CN | 102724929 | 10/2012 |
| CN | 103027762 A | 4/2013 |
| CN | 103347462 | 10/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 1 214 916 | 6/2002 |
| EP | 0 902 654 | 8/2004 |
| EP | 2 498 713 | 9/2012 |
| EP | 2 821 027 | 1/2015 |
| EP | 2 836 156 | 2/2015 |
| EP | 2 836 157 | 2/2015 |
| EP | 2 934 364 | 10/2015 |
| EP | 2 951 019 | 12/2015 |
| EP | 3 013 277 | 5/2016 |
| FR | 1 225 547 | 7/1960 |
| FR | 2 831 050 | 10/2001 |
| GB | 917 633 | 2/1963 |
| HK | 1 188 108 A | 4/2014 |
| IL | 219169 | 4/2013 |
| JP | 09-276292 | 10/1997 |
| JP | 10-33548 | 2/1998 |
| JP | 11-113927 A | 4/1999 |
| JP | 11-244303 A | 9/1999 |
| JP | 2000-254153 A | 9/2000 |
| JP | 2002-209911 | 7/2002 |
| JP | 2004-313659 | 11/2003 |
| JP | 3535685 B2 | 6/2004 |
| JP | 2004-261288 | 9/2004 |
| JP | 2005-095374 | 4/2005 |
| JP | 2007-533333 | 11/2007 |
| JP | 2008-93080 | 4/2008 |
| JP | 2008-132099 | 6/2008 |
| JP | 2009-114953 | 5/2009 |
| JP | 2013-544120 | 12/2013 |
| JP | 2015-510829 | 4/2015 |
| JP | 5902096 | 3/2016 |
| KR | 10-2008-0105713 A | 12/2008 |
| KR | 10-2012-0084897 A | 7/2012 |
| KR | 10-2013-0141103 A | 12/2013 |
| KR | 2004-72508 Y1 | 5/2014 |
| RU | 2326611 C1 | 12/2011 |
| WO | WO 1992/004871 | 4/1992 |
| WO | WO 1992/12685 | 8/1992 |
| WO | WO 1998/025536 | 6/1995 |
| WO | WO 1996/12447 | 5/1996 |
| WO | WO 1997/021420 | 6/1997 |
| WO | WO 1998/023219 | 6/1998 |
| WO | WO 2000/045731 | 8/2000 |
| WO | WO 2000/74587 | 12/2000 |
| WO | WO 2001/026577 | 4/2001 |
| WO | WO 2001/93773 | 12/2001 |
| WO | WO 2002/078644 | 10/2002 |
| WO | WO 2003/086223 | 10/2003 |
| WO | WO 2004/034923 | 4/2004 |
| WO | WO 2004/082501 | 9/2004 |
| WO | WO 2005/007008 | 1/2005 |
| WO | WO 2005/032393 | 4/2005 |
| WO | WO 2006/082101 | 8/2006 |
| WO | WO 2007/007335 | 1/2007 |
| WO | WO 2007/007336 | 1/2007 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/047670 | 4/2009 |
| WO | WO 2009/064947 | 5/2009 |
| WO | WO 2009/137815 | 11/2009 |
| WO | WO 2010/099538 | 9/2010 |
| WO | WO 2011/060327 | 5/2011 |
| WO | WO 2011/077291 | 6/2011 |
| WO | WO 2012/054905 | 4/2012 |
| WO | WO 2012/074918 | 6/2012 |
| WO | WO 2013/15700 | 1/2013 |
| WO | WO 2013/061251 | 5/2013 |
| WO | WO 2013/142385 | 9/2013 |
| WO | WO 2013/155492 | 10/2013 |
| WO | WO 2013/160888 | 10/2013 |
| WO | WO 2014/100751 | 6/2014 |
| WO | WO 2014/121293 | 8/2014 |
| WO | WO 2015/168329 | 11/2015 |
| WO | WO 2016/005221 | 1/2016 |

OTHER PUBLICATIONS

U.S. Appl. No. 61/894,762, filed Oct. 23, 2013, Lifshitz et al.
U.S. Appl. No. 61/895,316, filed Oct. 24, 2013, Lifshitz et al.
Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.
Al-Jadaa et al; Acoustic Hypochlorite Activation in Simulated Curved Canals; pp. 1408-1411; Journal of Endodontics, vol. 35, No. 10; Oct. 2009.
Anand et al; Prevention of Nozzle Wear in High-Speed Slurry Jets Using Porous Lubricated Nozzles; pp. 1-13; Department of Mechanical Engineering, The Johns Hopkins University, Oct. 2000.
Anantharamaiah et al; A simple expression for predicting the inlet roundness of micro-nozzles; pp. N31-N39; Journal of Micromechanics and Microengineering, vol. 17; Mar. 21, 2007.
Anantharamaiah et al; A study on flow through hydroentangling nozzles and their degradation; pp. 4582-4594; Chemical Engineering Science, vol. 61; May 2006.
Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.
Attin et al; Clinical evaluation of the cleansing properties of the nonistrumental technique for cleaning root canals; pp. 929-933; International Endodontic Journal, vol. 35, Issue 11; Nov. 2002.
Batchelor et al; Analysis of the stability of axisymmetric jets; pp. 529-551; Journal of Fluid Mechanics, vol. 14; Dec. 1962.
Begenir et al; Effect of Nozzle Geometry on Hydroentangling Water Jets: Experimental Observations; pp. 178-184; Textile Research Journal, vol. 74; Feb. 2004.
Begenir, Asli; The Role of Orifice Design in Hydroentanglement; Thesis submitted to North Carolina State University; dated Dec. 2002, in 107 pages.
Borkent et al; Is there gas entrapped on submerged silicon wafers? Visualizing nano-scale bubbles with cavitation; pp. 225-228; Solid State Phenomena, vol. 134 (2008); available online Nov. 2007.
Bremond et al; Cavitation on surfaces; pp. S3603-S3608; Journal of Physics: Condensed Matter, vol. 17; Oct. 28, 2005.
Brennen, Christopher E.; Fission of collapsing cavitation bubbles; pp. 153-166; Journal of Fluid Mechanics, vol. 472; Dec. 2002.
Chang et al; Effects of Inlet Surface Roughness, Texture, and Nozzle Material on Cavitation; pp. 299-317; Atomization and Sprays, vol. 16 (2006).
Culjat et al., "B-Scan Imaging of Human Teeth Using Ultrasound," Apr. 2003, in 4 pages.
Didenkulov et al; Nonlinear Acoustic Diagnostics of Scatterer Spatial Distribution in a Cavitation Jet; Nov. 19-23, 2001, pp. 276-278, XI Session of the Russion Acoustical Society.

(56) References Cited

OTHER PUBLICATIONS

Dumouchel, Christophe; On the experimental investigation on primary atomization of liquid streams; pp. 371-422; Experimental Fluids, vol. 45; Jun. 22, 2008.
Ebihara et al.: "Er:YAG laser modification of root canal dentine: Influence of pulse duration, repetitive irradiation and water spray," Lasers in Medical Science, 17(3), 198-207, Aug. 2002.
Eddingfield et al; Mathematical Modeling of High Velocity Water Jets; pp. 25-39; Proceedings of 1st U.S. Water Jet Conference; 1981.
EMS Electro Medical Systems, "Cleaning", in 2 pages, dated 2005, downloaded from http://www.ems-dent.com/en/endodontics cleaning. htm.
ESI Endo Soft Instruments, EMS Electro Medical Systems, Brochure in 2 pages, downloaded from www.emsdent.com, dated Jan. 2004.
European Extended Search Report re EP Application No. 09743801.4, dated Jun. 4, 2012.
European Extended Search Report re EP Application No. 14187012.1, dated Mar. 3, 2015, in 10 pages.
European Extended Search Report, dated Sep. 22, 2011, for EP Application No. 07755777.5, in 7 pages.
European Extended Search Report, re EP Application No. 08728345.3, dated Mar. 3, 2014.
European Extended Search Report, re EP Application No. 10830829.7, dated Oct. 21, 2015.
European Extended Search Report, re EP Application No. 11835265.7, dated Mar. 30, 2016, in 9 pages.
European Extended Search Report, re EP Application No. 13763534.8, dated Jan. 15, 2016.
European Extended Search Report, re EP Application No. 13775073.3, dated Nov. 3, 2015.
Feng et al; Enhancement of ultrasonic cavitation yield by multifrequency sonication; pp. 231-236; Ultrasonics Sonochemistry, vol. 9; Oct. 2002.
Flint, E. B., et al., "The Temperature of Cavitation", Science, vol. 253, Sep. 20, 1991, pp. 1397-1399.
Foldyna et al; Acoustic wave propagation in high-pressure system; pp. e1457-e1460; Ultrasonics vol. 44 (Supplement 1); Jun. 8, 2006.
Fuchs, "Ultrasonic Cleaning: Fundamental Theory and Application," Blackstone-Ney Ultrasonics, Jamestown, NY, May 2002.
G.E. Reisman and C.E. Brennen, "Pressure Pulses Generated by Cloud Cavitation", FED—vol. 236, 1996 Fluids Engineering Division Conference, vol. 1, pp. 319-328, ASME 1996.
G.E. Reisman, Y.-C. Wang and C.E. Brennen, "Observations of shock waves in cloud cavitation", J. Fluid Mech. (1998), vol. 355, pp. 255-283.
Ghassemieh et al; Effect of Nozzle Geometry on the Flow Characteristics of Hydroentangling Jets; pp. 444-450; Textile Research Journal, vol. 73; May 2003.
Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.
Hahn et al; Acoustic resonances in the bubble plume formed by a plunging water jet; pp. 1751-1782; Proceedings of the Royal Society of London A, vol. 459; May 16, 2003.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hydrocision Products: SpineJet Hydrosurgery; system webpage in 2 pages, copyright 2010, downloaded from http://www.hydrocision.com on Apr. 22, 2010.
Hydrocision SpineJet XL HydroSurgery System; Brochure in 2 pages, copyright 2004-2006, downloaded from http://www.hydrocision.com on Apr. 22, 2010.
International Preliminary Report and Written Opinion dated Nov. 9, 2010 for International Appl. No. PCT/US09/43386, in 6 pages.
International Preliminary Report on Patentability and Written Opinion, dated Oct. 14, 2014, re PCT Application No. PCT/US2013/036493, in 14 pages.
International Preliminary Report on Patentability dated Aug. 6, 2009, for International Appl. No. PCT/US08/52122, in 13 pages.
International Preliminary Report on Patentability dated Oct. 30, 2008, for International Appl. No. PCT/US07/09633, in 5 pages.
International Preliminary Report on Patentability re App. No. PCT/US2010/056620, dated May 15, 2012, in 10 pages.
International Preliminary Report on Patentability re PCT Application No. PCT/US2014/014732, dated Aug. 4, 2015.
International Preliminary Report on Patentability, re PCT Application No. PCT/US11/57401, dated Jan. 25, 2013 in 13 pages.
International Preliminary Report on Patentability, re PCT Application No. PCT/US2013/077286, dated Jun. 23, 2015, in 8 pages.
International Preliminary Report on Patentability, re PCT Application No. PCT/US2014/036451, dated Nov. 3, 2015, 2015, in 11 pages.
International Preliminary Report on Patentability, re PCT Application No. PCT/US2014/044186, dated Dec. 29, 2015, in 19 pages.
International Search Report and Written Opinion dated Apr. 11, 2008, for International Appl. No. PCT/US07/09633, in 8 pages.
International Search Report and Written Opinion dated Aug. 8, 2008, for International Appl. No. PCT/US08/52122, in 18 pages.
International Search Report and Written Opinion dated Jul. 29, 2009, for International Appl. No. PCT/US09/43386, in 8 pages.
International Search Report and Written Opinion from International Application No. PCT/US2011/057401, dated Jan. 30, 2012, in 20 pages.
International Search Report and Written Opinion dated Jun. 28, 2013, re PCT Application No. PCT/US2013/036493, in 21 pages.
International Search Report and Written Opinion re App. No. PCT/US2010/056620, dated Jan. 12, 2011, in 17 pages.
International Search Report and Written Opinion re App. No. PCT/US2014/014732, dated Jul. 18, 2014.
International Search Report and Written Opinion, re PCT Application No. PCT/US 13/32635, dated Jun. 17, 2013 in 14 pages.
International Search Report and Written Opinion, re PCT Application No. PCT/US2013/077286, dated May 27, 2014.
International Search Report and Written Opinion, re PCT Application No. PCT/US2014/044186, dated Jan. 21, 2015, in 19 pages.
International Search Report and Written Opinion, re PCT Application No. PCT/US2015/028360, dated Sep. 28, 2015, in 25 pages.
Jackson et al; Nozzle Design for Coherent Water Jet Production; pp. 53-89; Proceeding of the 2nd US Water Jet Conference; May 1983.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; In CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.

(56) References Cited

OTHER PUBLICATIONS

Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Maximum Dental Inc ., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Nammour et al.: "External temperature during KTP-nd:YAG laser irradiation in root canals: An in vitro study," Lasers in Medical Science, 19(1), 27-32, Jul. 2004.
Ohrn et al; Geometric Effects on Spray Cone Angle for Plain-Orifice Atomizers; pp. 253-268; Atomization and Sprays, vol. 1 (1991).
Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound ala carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sabeti, "Healing of apical periodontitis after endodontic treatment with and without obturation in dogs," Journal of Endodontics, Jul. 2006, pp. 628-633.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri, 1983.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Ulrich Schoop et al.: "The use of the erbium, chromium:yttrium-scandium-gallium-garnet laser in endodontic treatment: The results of an in vitro study," The Journal of the American Dental Association: vol. 138, Issue 7, Jul. 2007, pp. 949-955.
Wohlemuth et al.: "Effectiveness of GentleWave System in Removing Separated Instruments," JOE, vol. 41, No. 11, Nov. 2015.
Zuo et al; An Attribution of Cavitation Resonance: Volumetric Oscillations of Cloud; pp. 152-158; Journal of Hydrodynamics, vol. 21; Apr. 2009.
Ahmad et al., "Ultrasonic Debridement of Root Canals: Acoustic Cavitation and Its Relevance," Journal of Endontics, vol. 14, No. 10, pp. 486-493, Oct. 1988.
DiVito et al.: "Cleaning and debriding efficacy of new radial and stripped tips using an Erbium laser on human root canal dentin walls—an in vitro study: SEM observations," undated.
ADA American Dental Association, "Glossary of Dental Clinical and Administrative Terms," http://www.ada.org/en/publications/cdt/glossary-of-dental-clinical-and-administrative-ter, downloaded May 4, 2017, in 46 pages.
Lukac et al.: "Photoacoustic Endodontics Using the Novel SWEEPS Er:YAG Laser Modality," Journal of the Laser and Health Academy, vol. 2017, No. 1; www.laserlaserandhealth.com.
Schoop et al., "The Impact of an Erbium, Chromium: yttrium-scandium-gallium-garnet laser with radial-firing tips on endonic treatment," Lasers in Medical Science, Springer-Verlag, LO. vol. 24, No. 1,, Nov. 20, 2007.
Stamos et al., "Retreatodontics and ultrasonics", Journal of Endodontics, vol. 14., No. 1, pp. 39-42, Jan. 1, 1988.
Stamos et al., "Use of ultrasonics in single-visit endodontic therapy," Journal of Endodontics, vol. 13, No. 5, pp. 246-249, May 1, 1987.
Zehnder, "Root Canal Irrigants", Journal of Endodontics, vol. 32, No. 5, pp. 389-398, May 2006.

\* cited by examiner

FIG. 4
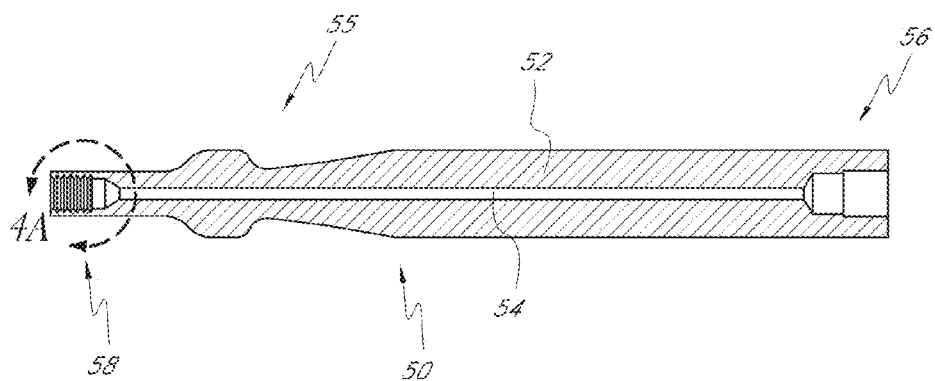
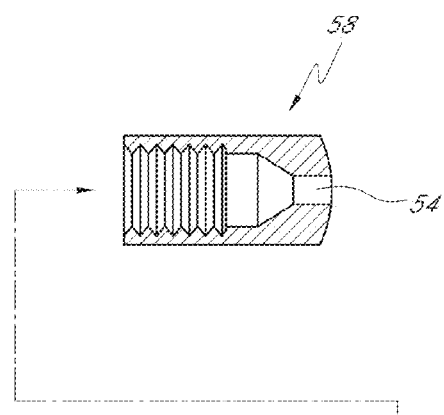
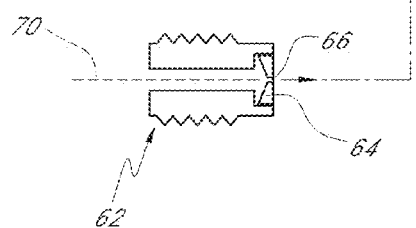
FIG. 4A

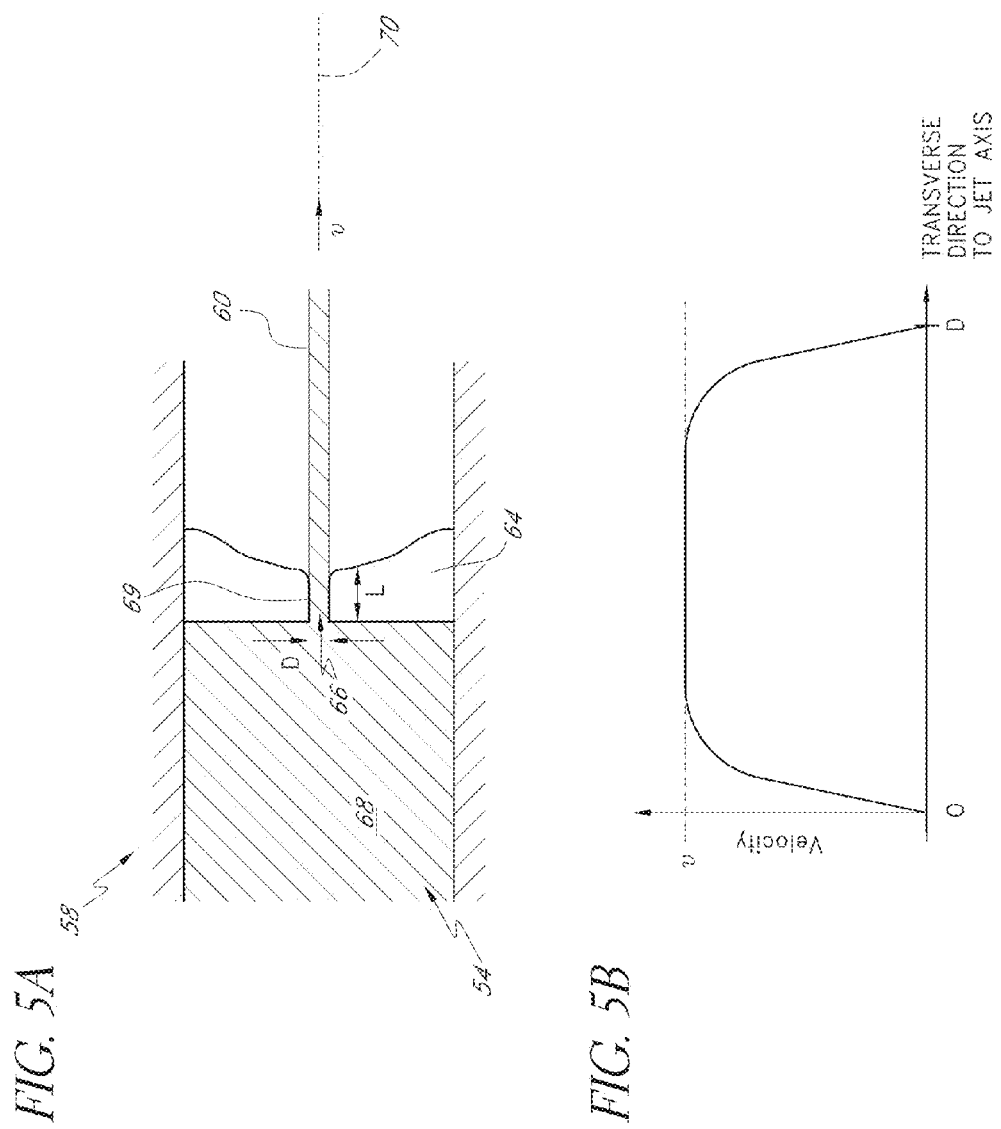

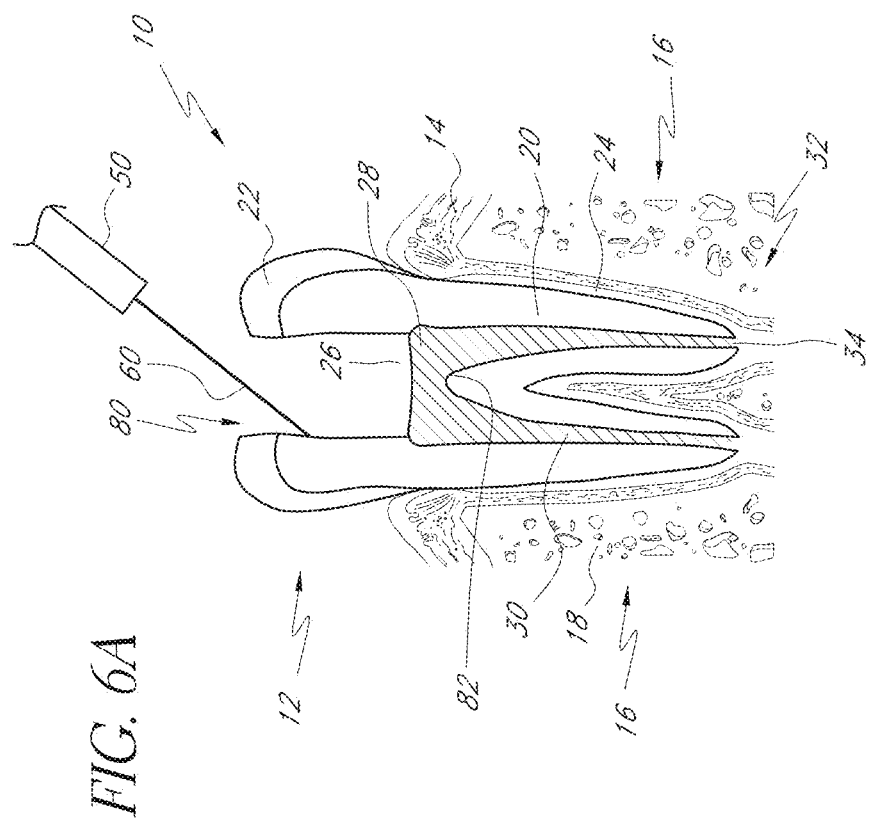

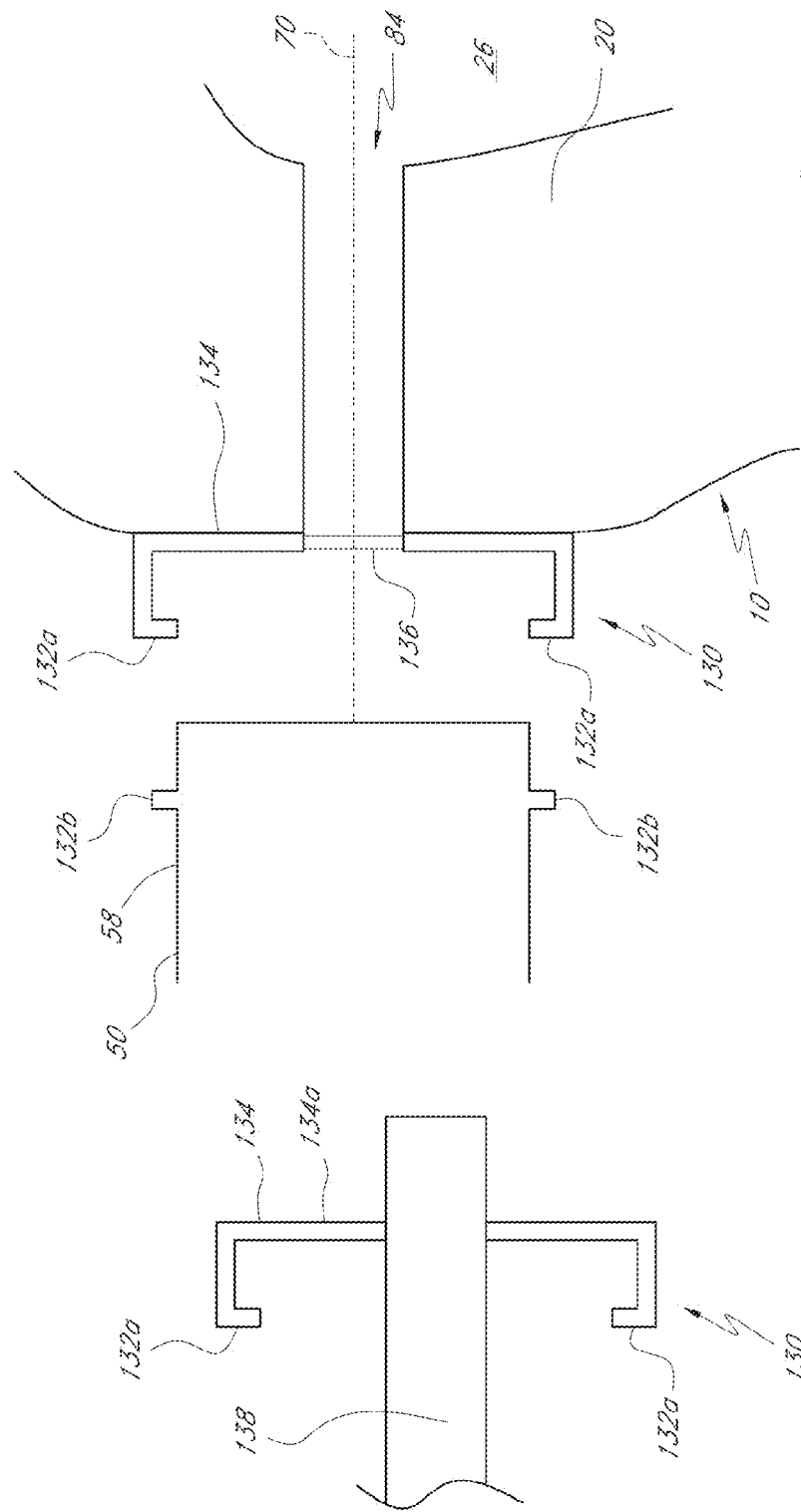

APPARATUS AND METHODS FOR TREATING ROOT CANALS OF TEETH

CROSS-REFERENCE TO RELATED APPLICATIONS

This application is a continuation of U.S. patent application Ser. No. 14/628,500, filed Feb. 23, 2015, entitled "APPARATUS AND METHODS FOR TREATING ROOT CANALS OF TEETH," which is a continuation of U.S. patent application Ser. No. 14/304,737, filed Jun. 13, 2014, entitled "APPARATUS AND METHODS FOR TREATING ROOT CANALS OF TEETH," which is a continuation of U.S. patent application Ser. No. 11/737,710, filed Apr. 19, 2007, entitled "APPARATUS AND METHODS FOR TREATING ROOT CANALS OF TEETH," which claims the benefit under 35 U.S.C. § 119(e) of U.S. Provisional Patent Application No. 60/793,452, filed Apr. 20, 2006, entitled "APPARATUS AND METHODS FOR TREATING ROOT CANALS OF TEETH," the entire contents of each of which is hereby incorporated by reference herein.

BACKGROUND

Field of the Disclosure

The present disclosure generally relates to methods and apparatus for removing organic matter from a body location and, more particularly, to methods and apparatus for removing organic matter from a root canal system of a tooth.

Description of the Related Art

In conventional root canal procedures, an opening is drilled through the crown of a diseased tooth, and endodontic files are inserted into the root canal system to open the canal and remove organic material therein. The root canal is then filled with solid matter such as gutta percha, and the tooth is restored. However, this procedure will not remove all organic material from all canal spaces. The action of the file during the process of opening the canal creates a smear layer of dentinal filings and diseased organic material on the dentinal walls, which is extremely difficult to remove. The organic material and necrotic tissue that remain in the canal spaces after completion of the procedure often result in post-procedure complications such as infections.

SUMMARY

In an embodiment, an apparatus for removing organic material from a root canal of a tooth is provided. The apparatus may comprise a liquid jet assembly having a liquid pressurization portion which pressurizes a liquid and a liquid beam forming portion in fluid communication with the pressurization portion. The beam forming portion may comprise an orifice that receives the pressurized liquid. The orifice may be sized and shaped to convert the pressurized liquid into a high velocity collimated beam that produces an acoustic wave upon impact with a surface of the tooth. The energy of the wave may cause organic material within the canal to be detached from the surrounding dentinal surface along a length of the canal. The length of the canal may extend at least to an apical portion of the tooth.

In another embodiment, a method of removing organic material that fills a root canal of a tooth is provided. The method comprises propagating an acoustic wave through the tooth. The method may also comprise detaching organic material filling the canal from the surrounding dentinal tissue using energy of the acoustic wave.

In another embodiment, a method of removing organic material from dentinal tubules which extend laterally from a root canal is provided. The method comprises introducing energy into a plurality of tubules through dentinal tissue such that at least a portion of an odontoblastic process within the tubules is detached from surrounding dentinal tissue and released from the tubule.

In another embodiment, a method for removing organic material from a root canal of a tooth is provided. The method comprises impacting dentin with an energy beam of a sufficiently high level to cause cavitations in fluid within the root canal. The cavitations maybe caused at least at locations in the root canal remote relative to the location of energy impact such that organic material within the canal may be detached from surrounding dentinal tissue.

In another embodiment, a method of removing organic material from a root canal comprises directing a liquid jet into the pulp chamber of a tooth through an opening in a side of the tooth at a substantial angle to the long axis of a root canal.

In another embodiment, a method of removing organic material from a root canal using a high velocity liquid jet is provided. The method comprises providing a handpiece for directing the liquid jet and positioning a contact member of the handpiece against a tooth to be treated. The method may also comprise using a sensor to sense contact of the contact member with the tooth. The method also may comprise activating the liquid jet only after the contact is sensed by the sensor.

In another embodiment, a method of removing organic material from a tooth is provided. The method comprises using acoustic energy to detach organic material from surrounding dentin within a plurality of root canals of a single tooth substantially simultaneously.

In another embodiment, an apparatus for removing organic material from a root canal of a tooth is provided. The apparatus comprises an acoustic energy generator arranged to couple acoustic energy to a dentinal surface of the tooth. The acoustic energy may be sufficient to cause organic material in the tooth to be detached from surrounding dentin at locations remote from the acoustic coupling surface.

In another embodiment, a method of removing organic material from a pulp cavity of a tooth is provided. The method comprises providing a liquid jet beam by passing liquid through an orifice. The method may also comprise using a positioning member to position the orifice relative to an opening into a pulp cavity of the tooth such that the jet beam passes through the opening.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

FIGS. 4 and 4A are cross-section views schematically illustrating an embodiment of a handpiece that can be used to maneuver the high-velocity liquid jet.

FIG. 5A is cross-section view schematically illustrating a distal end of an embodiment of a handpiece configured to deliver a high-velocity liquid jet.

FIG. 5B is a graph showing an example velocity profile of a coherent collimated jet.

FIG. 6A is a cross-section view schematically showing an endodontic method in which a high-velocity jet is directed toward dentin through an opening in the top of a tooth.

FIG. 6C is a cross-section view schematically illustrating an embodiment of a positioning member prior to adherence to a tooth.

FIG. 6D is a cross-section view schematically illustrating an embodiment of a positioning member adhered to a side of a tooth and used to assist coupling the distal end of the handpiece to the side of the tooth so that the high-velocity jet may be directed through the inlet opening.

FIG. 9A shows dentinal tubules in an apical area of a mature tooth magnified 1000×; FIGS. 9B and 9C show dentin and dentinal tubules magnified 1000× in an inclusion area of a juvenile tooth (FIG. 9B) and in a medial area of a mature root (FIG. 9C). A bar at the top left of each photo indicates the linear scale (in microns) for each photograph.

FIGS. 10A and 10C-10H are side views, and FIG. 10B is a partially exploded cross-section view.

DETAILED DESCRIPTION OF PREFERRED EMBODIMENTS

The present disclosure provides various apparatus and methods for dental treatments that overcome possible disadvantages associated with conventional root canal treatments. In certain embodiments, endodontic treatment methods (e.g., root canal therapy) comprise directing a high-velocity liquid jet toward a tooth. Impact of the jet causes acoustic energy to propagate from a site of impact through the entire tooth, including the root canal system of the tooth. The acoustic energy is effective at detaching substantially all organic material in the root canal system from surrounding dentinal walls. In many embodiments, the detached organic material can be flushed from the root canal using low-velocity irrigation fluid. As used herein organic material (or organic matter) includes organic substances typically found in healthy or diseased root canal systems such as, for example, soft tissue, pulp, blood vessels, nerves, connective tissue, cellular matter, pus, and microorganisms, whether living, inflamed, infected, diseased, necrotic, or decomposed.

Figure 1:
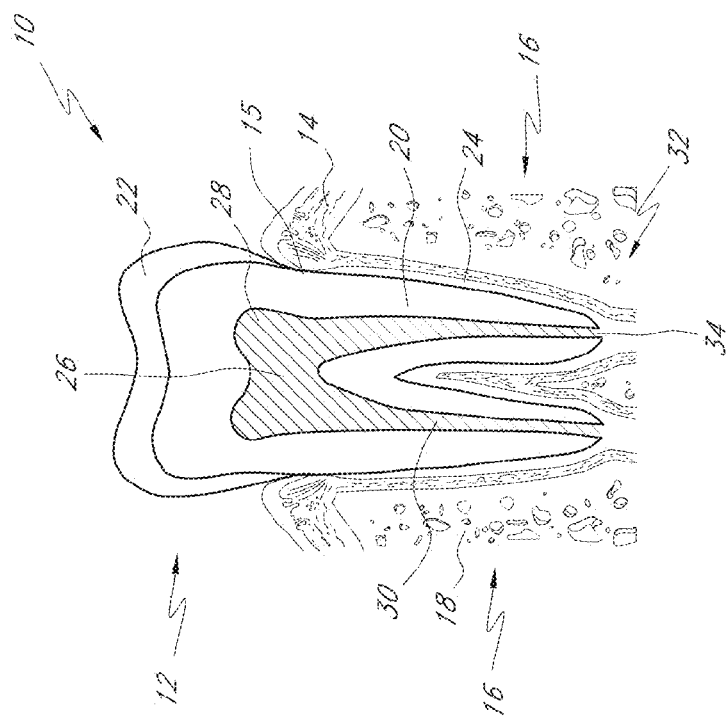
FIG. 1 is a cross-section view schematically illustrating a root canal system of a tooth.

FIG. 1 is a cross section schematically illustrating a typical human tooth 10, which comprises a crown 12 extending above the gum tissue 14 and at least one root 16 set into a socket (alveolus) within the jaw bone 18. Although the tooth 10 schematically depicted in FIG. 1 is a molar, the apparatus and methods described herein may be used on any type of tooth such as an incisor, a canine, a bicuspid, or a molar. The hard tissue of the tooth 10 includes dentin 20 which provides the primary structure of the tooth 10, a very hard enamel layer 22 which covers the crown 12 to a cementoenamel junction 15 near the gum 14, and cementum 24 which covers the dentin 20 of the tooth 10 below the cementoenamel junction 15.

A pulp cavity 26 is defined within the dentin 20. The pulp cavity 26 comprises a pulp chamber 28 in the crown 11 and a root canal space 30 extending toward an apex 32 of each root 16. The pulp cavity 26 contains dental pulp, which is a soft, vascular tissue comprising nerves, blood vessels, connective tissue, odontoblasts, and other tissue and cellular components. The pulp provides innervation and sustenance to the tooth through the epithelial lining of the pulp chamber 26 and the root canal space 30. Blood vessels and nerves enter/exit the root canal space 30 through a tiny opening, the apical foramen 32, near a tip of the apex 32 of the root 16.

Figure 2:
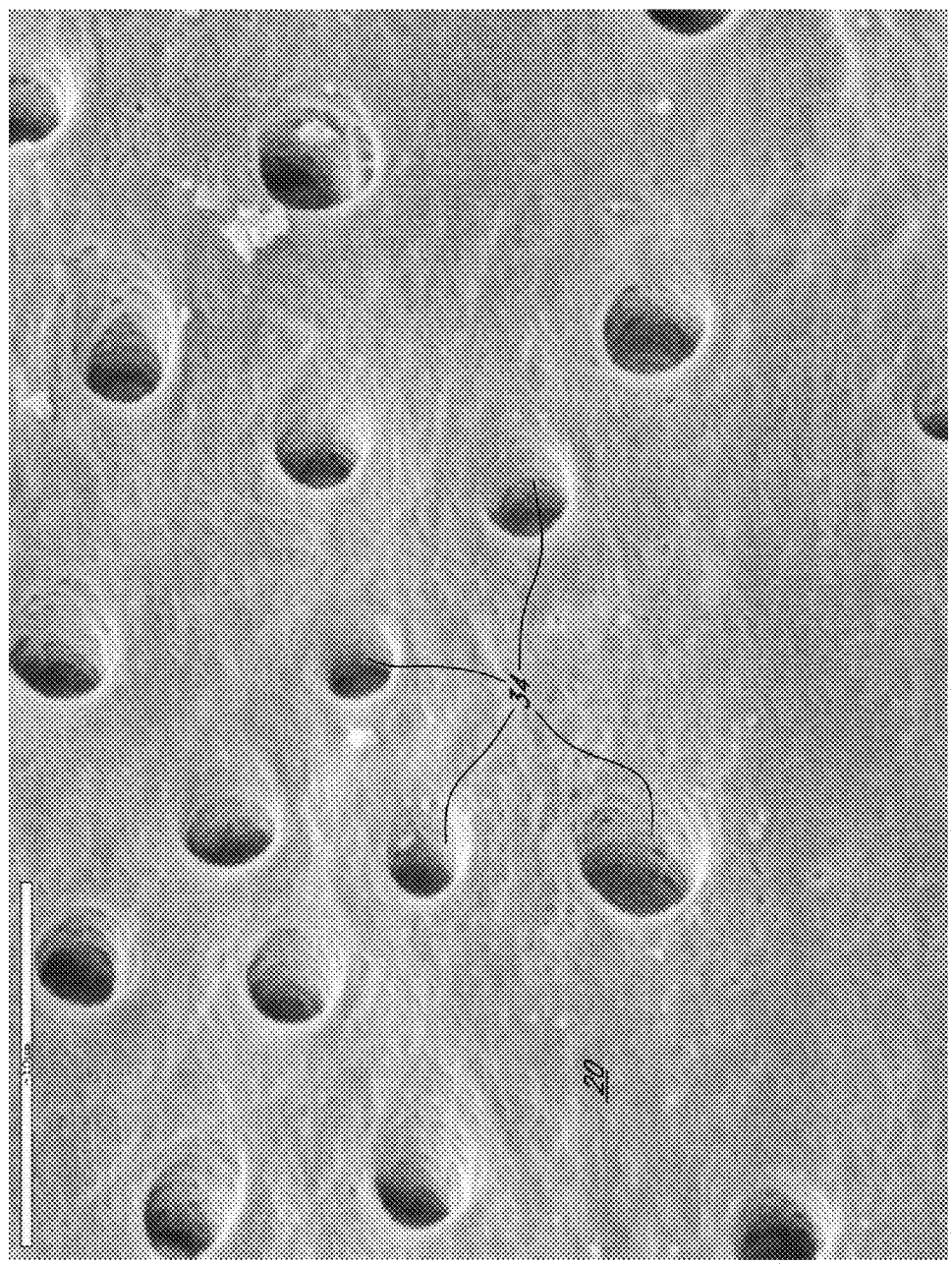
FIG. 2 is a scanning electron microscope photograph of a dentinal surface within a canal system in a tooth and shows numerous dentinal tubules on the dentinal surface.

FIG. 2 depicts a pulpal surface of the dentin 20. The dentin 20 comprises numerous, closely-packed, microscopic channels called dentinal tubules 34 that radiate outwards from the interior walls of the canal space 30 through the dentin 20 toward the exterior cementum 24 or enamel 22. The tubules 34 run substantially parallel to each other and have diameters in a range from about 1.0 to 3.0 microns. The density of the tubules 34 is about 5,000-10,000 per $mm^2$ near the apex 32 and increases to about 15,000 per $mm^2$ near the crown.

The dentin 20 is continuously formed by specialized cells called odontoblasts that secrete a mineralized substance that hardens into dentin. Odontoblasts form a single layer of cells between the dentin 20 and the pulp. An odontoblast has a cell body that is located on the pulpal surface of the dentin 20 on a tubule 34 and a cytoplasmic portion, called the odontoblastic process, that extends into and substantially fills the associated tubule 34. The odontoblasts are connected to each other with interodontoblastic collagen, and collagen fibrils may attach the odontoblast layer to the pulp. As a person ages, the odontoblasts continue to form dentin, which causes the root canal space 30 to decrease in diameter.

Figure 3:
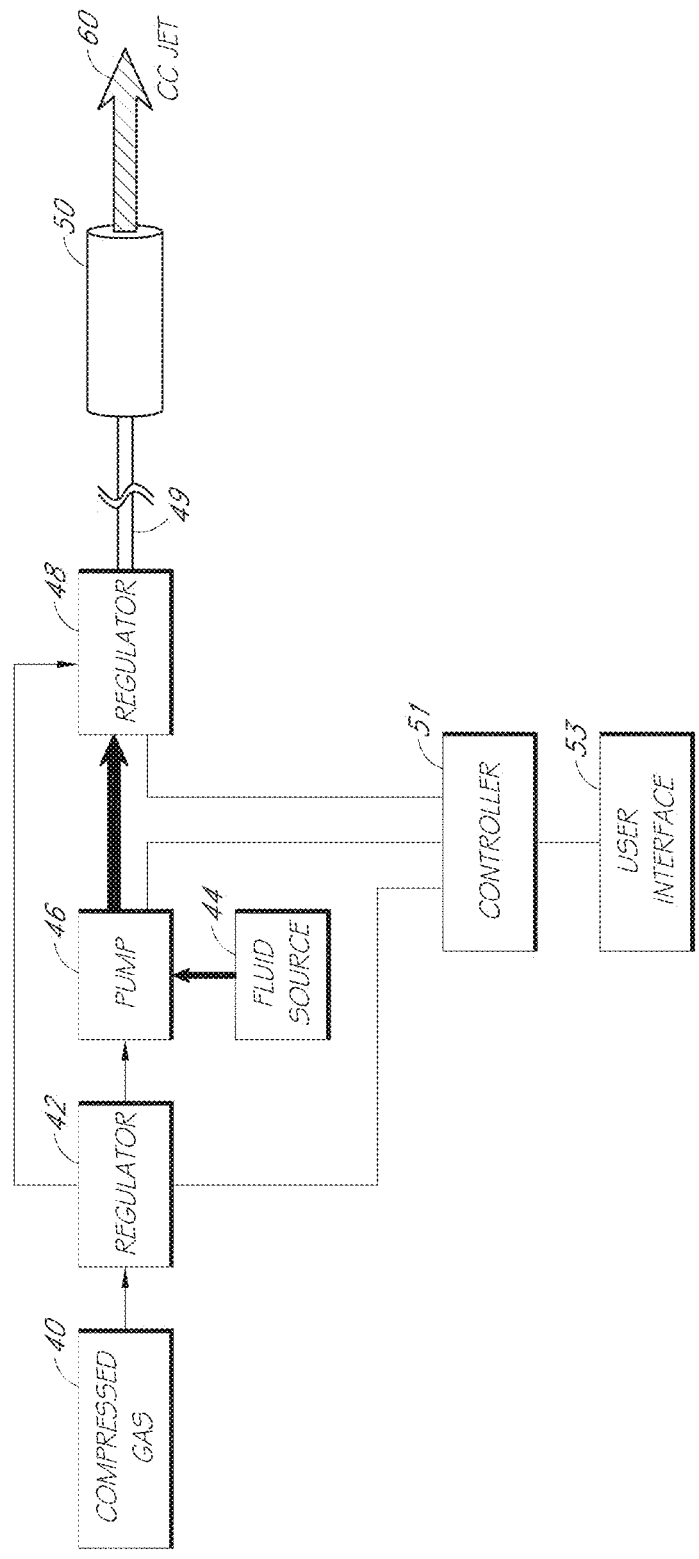
FIG. 3 is a block diagram schematically illustrating an embodiment of a compressor system adapted to produce a high-velocity liquid jet.

FIG. 3 is a block diagram that schematically illustrates a compressor system 38 adapted to generate a high-velocity jet of fluid for use in dental procedures. The compressor system 38 comprises a source of compressed gas 40 such as a pressurized air or gas source commonly available in dental service installations. The compressed gas 40 may be pressurized in a range from about 50 pounds per square inch (psi) to 150 psi including, for example, 100 psi. The compressed gas 40 may comprise any suitable commercially available gas including, for example, air, nitrogen, carbon dioxide, or a combination thereof. The compressed gas 40 is pneumatically connected to a pump 46 via a regulator 42. The regulator 42 can be used to regulate the pressure of the input gas to a desired pressure such as, for example, 40 psi. In some embodiments, the pump 46 comprises an air-driven hydraulic pressure intensifier that uses the compressed gas 40 to increase the pressure of liquid received from a fluid source 44. For example, a pressure intensifier having a 330:1 pressure intensification ratio can increase the pressure of the liquid to about 13,200 psi using pressurized gas at 40 psi from the regulator 42. Different pressure intensification ratios may be used in different embodiments. By adjusting the gas pressure with the regulator 42, the pressure of the liquid output from the pump 46 can be selectably adjusted to a desired value or range of values. In some embodiments, the pressure of the liquid can be adjusted within a range from about 500 psi to about 50,000 psi. In certain embodiment, it has been found that a pressure range from about 2,000 psi to about 11,000 psi produces jets that are particularly effective for endodontic treatments.

The fluid source 44 may comprise a fluid container (e.g., an intravenous bag) holding sterile water, a medical-grade saline solution, an antiseptic or antibiotic solution, a solution with chemicals or medications, or any combination thereof. More than one fluid source may be used. In certain embodiments, it is advantageous for jet formation if the liquid provided by the fluid source 44 is substantially free of dissolved gases (e.g., less than 0.1% by volume) and particulates, which can act as nucleation sites for bubbles. In some embodiments, the fluid source 44 comprises degassed distilled water. A bubble detector (not shown) may be disposed between the fluid source 44 and the pump 46 to detect bubbles in the liquid and/or to determine whether liquid flow from the fluid source 44 has been interrupted or the container has emptied. The liquid in the fluid source 44 may be at room temperature or may be heated and/or cooled to a different temperature. For example, in some embodiments, the liquid in the fluid source 44 is chilled to reduce the temperature of the high velocity jet generated by the compressor system 38.

In the embodiment depicted in FIG. 3, the high-pressure liquid from the pump 46 is fed to a regulator 48 and then to a handpiece 50, for example, by a length of high-pressure tubing 49. The regulator 48 may be operable with compressed gas from the source 40 and may be used to regulate the pressure of the liquid to a desired value. For example, in one embodiment, the regulator 48 reduces the 13,200 psi pressure from the pump 46 to about 12,000 psi. The regulator 48 may include water pressure sensors and bleed-off valves (e.g., an air-driven needle valve) to provide the desired pressure and to permit an operator to actuate/deactuate water jet output from the handpiece 50.

The handpiece 50 receives the high pressure liquid and is adapted at a distal end to generate a high-velocity, coherent, collimated beam or jet 60 of liquid for use in dental procedures. The handpiece 50 may be sized and shaped to be maneuverable so that the jet 60 may be directed toward or away from various portions of the tooth 10.

The compressor system 38 may include a controller 51 that controls the operation of the components of the system 38. The controller 51 may comprise a microprocessor, a special or general purpose computer, a floating point gate array, and/or a programmable logic device. In one embodiment, the controller 51 is used to operate the regulators 42, 48 and the pump 46 so that the high-pressure liquid delivered to the handpiece 50 is at a suitable working pressure. The controller 51 may also be used to control safety of the system 38, for example, by limiting system pressures to be below safety thresholds and/or by limiting the time that the jet 60 is permitted to flow from the handpiece 50. In certain embodiments, the controller 51 may be used to vary or cycle the pressure of the liquid delivered to the handpiece 50, for example, by cycling pressures provided by one or both of the regulators 42, 48. In certain such embodiments, sinusoidal or sawtooth pressure variability may be used to provide corresponding variability in the speed of the jet 60. In certain embodiments, cycle time for the pressure variability may be in a range from about 0.1 seconds to about 5 seconds. Additionally and optionally, the controller 51 may regulate a pulse intensifier device (not shown), such as a piezoelectric transducer, that causes pulsations in the jet 60. For example, in certain embodiments, the jet 60 comprises a pulsed jet, which may include a series of discrete liquid pulses, a continuous stream of fluid having spatially varying pressure, velocity, and/or area, or a combination thereof. The controller 51 advantageously may control the amplitude and frequency of the pulsations in the jet 60. In certain embodiments, the amplitude of the pressure variation may be in a range from several hundred to several thousand psi. The pulse frequency may be in a range from about 0.1 Hz to about 10 MHz. For example, in some embodiments, a pulse frequency of about 1 MHz is applied to produce a jet comprising a series of droplets.

The system 38 may also include a user interface 53 that outputs relevant system data and accepts user input. In some embodiments, the user interface 53 comprises a touch screen graphics display. In some embodiments, the user interface 53 may display information including the working liquid pressure in the handpiece 50 and instructions and/or procedures for operating on different tooth types (e.g., incisors, bicuspids, or molars). The user interface 53 may accept user input such as a time setting that sets a maximum time during which the compressor system 38 will deliver the jet 60 and other useful endodontic treatment options. For example, some embodiments permit an operator to select a "ramp up" and/or "ramp down" option in which the working liquid pressure can be gradually increased or decreased, respectively. The ramp up option advantageously may be used for initial aiming of the jet 60 towards a suitable portion of the tooth 10, while the ramp down advantageously may be used if the jet 60 is moved toward a sensitive portion of the tooth 10 (e.g., the apex 32). The compressor system 38 may also include a storage medium (e.g., volatile or nonvolatile memory) configured to store system operating information and executable instructions, user preferences, preferred operating pressures and times, patient data, etc. In some embodiments, the storage medium comprises on-board memory of the controller 51 and/or additional random access or read-only memory, flash memory, removable memory cards, etc.

The compressor system 38 may include additional and/or different components and may be configured differently than shown in FIG. 3. For example, the system 38 may include an aspiration pump that is coupled to the handpiece 50 (or an aspiration cannula) to permit aspiration of organic matter from the mouth or tooth 10. In other embodiments, the compressor system 38 may comprise other pneumatic and/or hydraulic systems adapted to generate the high-velocity beam or jet 60. For example, certain embodiments may utilize apparatus and systems described in U.S. Pat. No. 6,224,378, issued May 1, 2001, entitled "METHOD AND APPARATUS FOR DENTAL TREATMENT USING HIGH PRESSURE LIQUID JET," and/or U.S. Pat. No. 6,497,572, issued Dec. 24, 2002, entitled "APPARATUS FOR DENTAL TREATMENT USING HIGH PRESSURE LIQUID JET," the entire disclosure of each of which is hereby incorporated by reference herein.

Moreover, in other embodiments, the high-velocity jet 60 may be generated by systems other than the high-pressure compressor system 38, such as, for example, by a pump system. In one such embodiment, an electric motor drives a pump that is in fluid communication with a liquid reservoir. The pump increases the velocity of the liquid so as to provide a narrow beam of high-velocity liquid from the handpiece 50. In some embodiments, multiple pumps are used. As is well known from Bernoulli's law, the total pressure in a flowing fluid includes static (e.g., thermodynamic) pressure plus dynamic pressure (associated with fluid kinetic energy). A skilled artisan will recognize that static pressures in motor-driven pump systems may be less than static pressures in compressor systems, because the motor-driven pump primarily increases the dynamic pressure (e.g., the fluid velocity) of the liquid. The total pressures (static plus dynamic) achieved are comparable in many embodiments of compressor systems and pump systems.

FIGS. 4 and 4A are cross-section views that schematically illustrate one embodiment of the handpiece 50 adapted for forming the high-velocity jet 60. The handpiece 60 comprises an elongated tubular barrel 52 having a central passageway 54 extending axially therethrough. The handpiece 50 has a proximal end 56 that is adapted to engage tubing from the regulator 48 in order for the passageway 54 to be in fluid communication with the high pressure liquid delivered by the compressor system 38. The barrel 52 may include features 55 that enhance grasping the handpiece with the fingers and thumb of the operator. A distal end 58 of the barrel 52 (shown in closeup in FIG. 4A) includes a threaded recess adapted to engage complementary threads of an orifice mount 62, which is configured to hold an orifice jewel 64 at an end thereof. The orifice mount 62 is tightly screwed into the distal end 58 of the barrel 52 to secure the orifice jewel 64 adjacent to a distal end of the passageway 52.

The orifice jewel 64 may comprise a circular, disc-like element having a small, substantially central orifice 66 formed therein. The orifice jewel 64 may be fabricated from a suitably rigid material that resists deformation under high pressure such as, for example, synthetic sapphire or ruby. The orifice mount 62 advantageously secures the orifice jewel 64 substantially perpendicular to the passageway 54 so that high pressure liquid in the passageway 54 can flow through the orifice 66 and emerge as a highly collimated beam of fluid traveling along a longitudinal jet axis 70 that is substantially coaxial with the barrel 52 of the handpiece 50. In some embodiments, the distal end 58 of the handpiece 50 may include additional components, for example, to assist guiding or directing the jet 60 and/or to provide aspiration. Also, as further described below, the distal end 58 of the handpiece 50 may be adapted to receive various end caps that assist guiding the jet 60 toward the pulp cavity 26.

FIG. 5A is a cross-section schematically illustrating the distal end 58 of an embodiment of the handpiece 50 to further illustrate formation of the jet 60. The orifice jewel 64 is secured at the distal end of the handpiece 50 and forms a tight seal to prevent leakage of high-pressure liquid 68 contained in the passageway 54. In the depicted embodiment, the orifice jewel 64 has a proximal side that is substantially flat and a distal side that is concave (e.g., thinnest near the orifice 66). The orifice 66 has a substantially circular cross-section with a diameter "D." The axial length of sides 69 of the orifice 66 is "L." The diameter D may be in a range from about 5 microns to about 1000 microns. Other diameter ranges are possible. In various embodiments, the diameter D may be in a range from about 10 microns to about 100 microns, a range from about 100 microns to about 500 microns, or range from about 500 microns to about 1000 microns. In various preferred embodiments, the orifice diameter D may be in a range of about 40-80 microns, a range of about 45-70 microns, or a range of about 45-65 microns. In one embodiment, the orifice diameter D is about 60 microns. The ratio of axial length L to diameter D may be about 50:1, 20:1, 10:1, 5:1, 1:1, or less. In one embodiment, the axial length L is about 500 microns. In certain embodiments, the ratio of axial length L to diameter D is selected so that transverse width of any boundary layers that may form on the sides 69 of the orifice 66 have a transverse width that is sufficiently small, for example, much less than the diameter D. In preferred embodiments, the orifice diameter is 40-80 microns, and more preferably 45-70 microns, and even more preferably 45-65 microns. The axial length of the orifice is preferably no greater than ten times the diameter of the orifice, and the liquid pressure at the input side of the orifice is 7,000 to 15,000 psi. In one embodiment, the orifice is about 60 microns in diameter, the axial length of the orifice about 500 microns, and the liquid pressure at the input side of the orifice about 11,000 psi. Since the output side of the orifice is at atmospheric pressure, the pressure drop at the orifice will be only slightly less than the pressure at the input side of the orifice. This combination of parameters provides a high velocity, high momentum, collimated, coherent liquid beam that is efficacious for cleaning without significant dentinal erosion.

In certain embodiments, the sides 69 of the orifice 66 are machined, polished, or otherwise processed to be substantially smooth in order to reduce or prevent formation of turbulence, cavitation, bubbles, fluid instabilities, or other effects that may interfere with substantially smooth, laminar flow of the liquid through the orifice 66. For example, in certain such embodiments, the sides 69 have a root-mean-square (rms) surface roughness less than about 10 microns, less than about 1 micron, or less than about 0.1 microns. In other embodiments, the rms surface roughness is much smaller than the diameter D of the orifice such as, for example, less than about 0.1 D, less than about 0.01 D, less than about 0.001 D, or less than about 0.0001 D. Additionally, highly demineralized liquids may be used to reduce buildup of impurities along the sides 69, which advantageously may increase the useful operating lifetime of the orifice jewel 64.

As schematically depicted in FIG. 5A, the high pressure liquid 68 in the passageway 54 emerges through the orifice 66 as a high-velocity, collimated jet 60 traveling substantially along the jet axis 70 with a velocity, v. In some embodiments of the compressor system 38, the jet velocity is estimated to be proportional to $(P/\rho)^{1/2}$, where P is the liquid pressure in the passageway 54 and p is the density of the liquid. In certain embodiments, water pressurized to about 10,700 psi emerges from the orifice as a jet 60 having a velocity of about 220 m/s. By adjusting the liquid pressure delivered by the compressor system 38, the handpiece 50 can deliver jets having different velocities. In some embodiments, the user interface 53 permits the operator to selectively adjust system pressures so that the velocity of the jet is suitable for a particular dental treatment.

In certain embodiments of the system 38, the liquid used to form the jet 60 is substantially free from dissolved gases (e.g., less than about 0.1% per volume). If the dissolved gas content of the liquid is too high, bubbles may formed at the nozzle orifice 66 due to the pressure drop. Additionally, the pressure drop should preferably be sufficiently low to prevent formation of vapor at the distal end of the orifice 66.

The presence of substantial vapor, gas or bubbles, or particle contaminants in the liquid may cause a significant portion of the energy of the liquid jet 60 to be depleted, and there may be insufficient kinetic energy (and/or momentum) to provide efficient cleaning of the root canal system. When used for removing tissue and/or organic matter from root canals, the effectiveness of the device disclosed in U.S. Pat. No. 6,497,572, issued Dec. 24, 2002, and entitled "Apparatus for Dental Treatment Using High-Pressure Liquid Jet," is significantly increased by using liquids that are free (or at least substantially free) of dissolved gases (as well as bubbles) to form the high-velocity jet. Preferably, the liquid is bubble-free distilled water, and the concentration of dissolved gases is no more than e.g. 0.1% by volume. In use, the liquid beam is preferably directed at the floor of the pulp chamber at an oblique angle relative to the long axis of the root canals. Although the chamber fills with liquid, the beam has sufficient velocity to impact the submerged dentin with great force. Upon impingement, the primary, collimated coherent beam from the jet apparatus generates a high-energy acoustic pressure wave that propagates along the body of the tooth. At the dentinal surfaces of the main and side canals, the acoustic wave causes any surrounding liquid to cavitate. This cavitation is a surface effect cavitation caused by conversion of the water (or other liquid) from a liquid state to a vapor state. Due to the high energy required for such conversion, collapse of the cavitation bubble occurs with great force against the surface of the dentin and cleans through creation of cavitation-induced sub-jets which radiate inward toward the surface from the point of collapse of the cavitating vapor. The substantially gas-free liquid is preferred for the above described cavitation process. If the dissolved gas content of the liquid is too high, bubbles will be formed at the nozzle orifice due to the pressure drop. Additionally, the pressure drop should preferably be sufficiently low to prevent formation of vapor at the nozzle orifice. The presence of significant vapor, gas or bubbles causes much of the energy of the beam to be depleted, and there will be insufficient energy to generate the liquid to vapor-phase cavitation, which is a surface effect.

The jet 60 emerges from the distal end of the orifice 66 as a beam of fluid traveling substantially parallel to the jet axis 70. Such jets are called "collimated" jets. In certain embodiments, the angular divergence of the jet 60 is less than about 1 degree, less than about 0.1 degree, or less than about 0.01 degree. In other embodiments, jet beams with different angular divergences may be used. In some embodiments, the jet 60 can travel as a collimated beam for a distance of about 1 to 3 inches before the jet 60 begins to disperse (e.g., due to entrainment of air). In certain embodiments, the jet 60 may travel a distance at least several thousand times the jet diameter D before beginning to disperse.

As described above, it may be advantageous for the sides 69 of the orifice 66 to be sufficiently smooth that liquid flows through the orifice 66 in a substantially laminar manner. In certain embodiments, the transverse width of any boundary layers formed along the sides 69 of the orifice 66 is much smaller than the diameter D, and, away from the boundary layers, the speed of the jet 60 is substantially constant across the width of the orifice. FIG. 5B is a graph schematically illustrating an example velocity profile of the jet 60 after it has emerged from the distal end of the orifice 66. The graph depicts flow velocity in the direction of the jet axis 70 versus a distance transverse (e.g., orthogonal) to the jet axis 70. In this example embodiment, away from narrow boundary layers near the outer surface of the jet 60 (e.g., near 0 and D on the graph), the jet velocity is substantially constant across the width of the jet. Jets having substantially constant velocity profiles are called "coherent" jets. In other embodiments, the velocity profile of the jet 60 is not substantially constant across the width of the jet 60. For example, the jet velocity profile in certain embodiments is a parabolic profile well-known from pipe flow.

In certain embodiments, the compressor system 38 is configured to deliver a coherent, collimated jet 60 of high-velocity liquid. A coherent, collimated jet will be denoted herein as a "CC jet." The following example provides various representative properties of a CC jet 60 that can be generated using an embodiment of the system 38. In this example system, the diameter D and the axial length L of the orifice 66 are 60 microns and 500 microns, respectively. In one embodiment, the pressure of the liquid (degassed, distilled water) in the handpiece 50 is about 8,000 psi, which produces a jet velocity of about 190 m/s. The mass discharge rate of the jet is about 0.5 g/s, and the jet can produce a force of about 0.1 Newton when impacting a surface at normal incidence. The jet provides a kinetic power of about 10 Watts. If the jet is directed toward a tooth for about 10 seconds, the jet can deliver a momentum (or impulse) of about 1 kg m/s and an energy of about 100 Joules (about 23 calories).

In other embodiments, the CC jet is produced from liquid pressurized to about 2500 psi. The jet velocity is about 110 m/s, and volume flow rate is about 0.3 mL/s. The CC jet can produce about 2 W of kinetic power. The jet 60 may remain substantially collimated over propagation lengths from about 1 cm to about 30 cm in various embodiments.

The energy flux produced by the liquid jet is the kinetic power of the jet divided by the transverse area of the jet beam. The energy flux may be in a range from about 1 kW/cm$^2$ to about 1000 kW/cm$^2$. In some embodiments, the energy flux is in a range from about 50 kW/cm$^2$ to about 750 kW/cm$^2$, including, for example, 70 kW/cm$^2$, 175 kW/cm$^2$, 350 kW/cm$^2$, and 550 kW/cm$^2$. In one experiment, a CC jet was directed toward a dentinal surface of a tooth, and widespread acoustic noise (possibly due to acoustic cavitation) was detected in the tooth when the energy flux of the jet exceeded about 75 kW/cm$^2$. At the onset of detectable acoustic noise, the CC jet had the following properties: velocity of about 110 m/s, kinetic power of about 2 W, and mass flow rate of about 0.3 g/s. The pressure producing the CC jet was about 2500 psi.

By using different fluid working pressures and/or orifice diameters, jets having different properties can be generated. For example, in certain embodiments, the mass discharge rate may be in a range from about 0.01 g/s to about 1 g/s, the jet velocity may be in range from about 50 m/s to about 300 m/s, the jet force may be in a range from about 0.01 N to about 1 N, and the jet power may be in a range from about 0.1 W to about 50 W. In various endodontic treatments, the jet is applied to a tooth for a time in a range from about 1 second to 120 seconds. Accordingly, in such treatments, the jet can deliver momentum (or impulse) in a range of about 0.01 kg m/s to about 100 kg m/s, and energy in a range of about 0.1 J to about 500 J. In some embodiments, an energy range from about 20 J to about 400 J may be effective at providing cleaning of the root canal system without causing substantial erosion of dentin. A person of ordinary skill will recognize that the compressor system 38 can be configured to provide liquid jets having a wide range of properties that may be different from the example values and ranges provided herein, which are intended to be illustrative and non-limiting.

In various dental treatments, the compressor system 38 delivers a jet 60, which advantageously may be a CC jet, that is directed toward one or more portions of a tooth in order to, for example, excise and/or emulsify organic material, provide irrigation, and/or generate acoustic energy for delaminating organic matter from the pulp cavity 26.

FIG. 6A schematically illustrates one embodiment of an endodontic treatment for diseased pulp in the tooth 10. A drill or grinding tool is initially used to make an opening 80 in the tooth 10. The opening 80 may extend through the enamel 22 and the dentin 20 to expose and provide access to pulp in the pulp cavity 26. The opening 80 may be made in a top portion of the crown 12 of the tooth 10 (as shown in FIG. 3) or in another portion such as a side of the crown 12 or in the root 16 below the gum 14. The opening 80 may be sized and shaped as needed to provide suitable access to the diseased pulp and/or some or all of the canal spaces 30. In some treatment methods, additional openings may be formed in the tooth 10 to provide further access to the pulp and/or to provide dental irrigation.

The handpiece 50 may be used to deliver a jet 60 of liquid to a portion of the tooth 10. The jet 60 advantageously may, but need not, be a CC jet. The jet 60 can be used to cut through organic material in the pulp chamber 28. Additionally, as will be further described below, the jet 60 may be directed toward hard surfaces of the tooth 10 (e.g., the dentin 20) to generate acoustic energy, which may propagate through the dentin 20, the dentinal tubule, and the organic material in the root canal space 30. The acoustic energy causes detachment of organic material from the dentin 20 without requiring that the jet directly impact the organic material. In certain embodiments, the acoustic energy has been found to be effective in causing detachment of the entire body of pulp (and other organic material) from within the pulp chamber 28 and/or root canal space 30, without the use of endodontic files. The jet 60 preferably should have insufficient energy, energy flux, and/or momentum to damage or substantially erode the dentin 20.

In some treatment methods, the operator can maneuver the handpiece 50 to direct the jet 60 around the pulp chamber 28 during the treatment process. The distal end of the handpiece 50 may be held about 1 inch from the tooth 10 so that the liquid impacts a portion of the tooth 10 as a substantially collimated coherent beam. The jet 60 may provide sufficient force to cut through and/or emulsify some or all of the organic material in the pulp chamber 28. The flow of liquid from the jet 60 may create sufficient swirling or turbulent flow to remove the cut and/or emulsified organic material from the pulp cavity 26 so that it can be aspirated from the mouth of the patient. In other treatment embodiments, pulpal tissue in the pulp chamber 28 may be removed via conventional techniques prior to (and/or during) liquid jet treatment to expose a portion of the dentin 20. The jet 60 may then be directed to the exposed portion.

Figure 7:
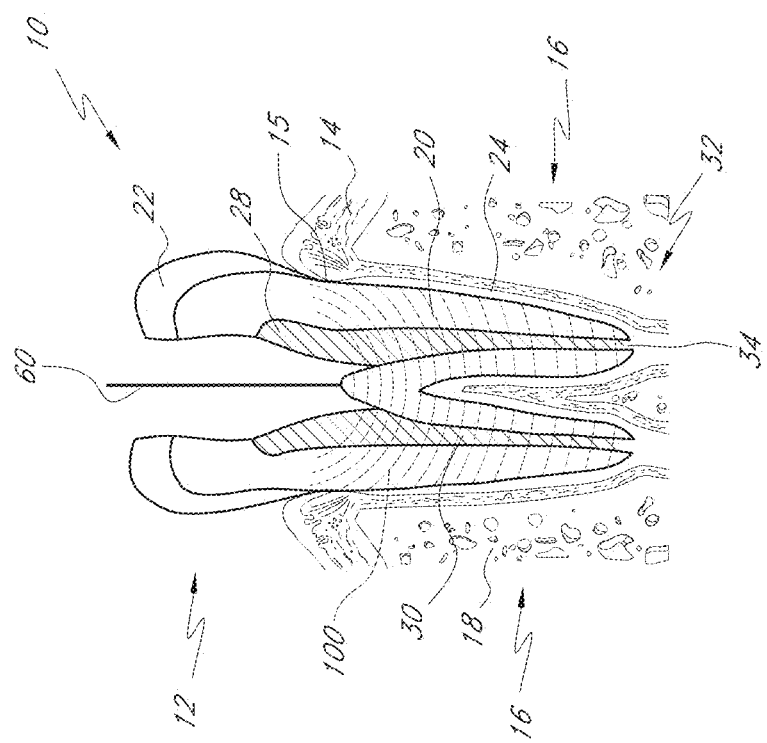
FIG. 7 schematically illustrates production of an acoustic wave caused by impingement of a high-velocity liquid jet onto a dentinal surface.

The jet 60 may be directed toward the floor 82 of the pulp chamber 28 (see, e.g., FIG. 7). In some methods, the jet 60 is directed toward the floor 82 (and/or walls) of the pulp chamber 28 advantageously at a substantial angle (e.g., 15-50 degrees) relative to the long axis of the root canal space 30 to ensure that the jet does not directly impact the apical portion of the canal space 30, thereby reducing a possibility that the force (and/or pressure) imparted by the jet 60 will cause damage to healthy tissue around the apical foramen 34. Accordingly, certain disclosed treatment methods advantageously may be used on "open apex" teeth having underdeveloped and/or enlarged apices, because impingement of the jet 60 in the pulp chamber 28 will not harm the periapical portion of the tooth 10. Additionally or optionally, the jet 60 can be directed toward one or more sides of the pulp chamber 28 so as to impact the dentin 20. In some embodiments, the jet is directed to several locations in or on the tooth 10. An advantage of some methods is that the impact of the jet 60 on the dentin 20 does not cause significant erosion or destruction of the dentin 20 within the tooth 10. Accordingly, such methods may be minimally invasive in comparison with conventional root canal procedures.

The pulp cavity 26 may fill with fluid during the treatment. For sufficiently high working pressures, the jet 60 will have sufficient velocity to impact submerged dentin 20 with enough force to provide effective treatment. In certain embodiments of the treatment method, one or more properties of the jet 60 are temporally varied during the treatment. For example, the working pressure may be varied to ramp up or ramp down the jet velocity or to cause the jet to alternate between high-speed flow and low-speed flow. The jet 60 may comprise a pulsed jet with pulsation amplitude and/or frequency selected to provide effective treatment. A combination of the above treatment methods may be used, serially or in alternation.

As noted above, detachment of the organic material within the root canal system from the surrounding dentin 20 does not require that the jet 60 impact the organic material in the root canal space 30. Rather, the jet 60 may be directed against a dentinal wall (e.g., in the pulp chamber 28), which couples acoustic energy to the tooth 10 so as to cause detachment of the organic material. In some methods, the detachment occurs relatively quickly after the jet 60 impinges on the dentinal wall (e.g., within a few seconds) and may occur substantially simultaneously throughout one or more root canal spaces 30 of the tooth 10.

Figure 6B:
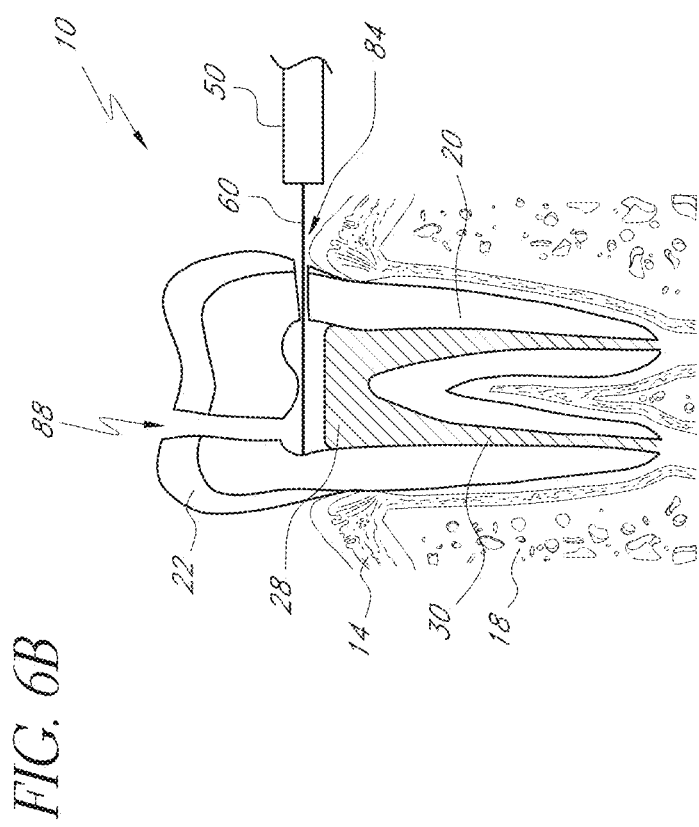
FIG. 6B is a cross-section view schematically showing another endodontic method in which the high-velocity jet is directed toward the dentin through an inlet opening in a side of the tooth and a relief opening in the top of the tooth is provided to reduce pressure buildup, if present, and to permit debridement.

In one presently preferred method schematically illustrated in FIG. 6B, the jet beam 60 is introduced into an inlet opening 84 formed in the side (e.g., buccal or lingual surface) of the tooth 10 with a conventional dental drill. The opening 84 may be formed near the cementoenamel junction 15. In some procedures, a portion of the gum 14 is depressed to provide access to the intended position of the opening 84 near the cementoenamel junction 15. The opening 84 may have a diameter in a range from about 1 mm to about 2 mm and may extend from the exterior surface of the tooth 10 to the pulp chamber 28. In some embodiments, the diameter is about 1.2 mm. Different diameters may be used in other embodiments. The opening 84 is thus generally transverse to the long axis of any root canal space 30 and ensures that the energy of the jet 60 will not be directed down any canal spaces 30. A benefit of providing the opening 84 in the side of the tooth 10 is that less hard tissue of the tooth 10 is damaged than if the opening were formed through the occlusal surface of the tooth 10. Although it is presently preferred to use a single inlet opening 84 to reduce invasiveness of the procedure, in other methods, two or more inlet openings may be used.

FIGS. 6C and 6D are cross-section views schematically illustrating an embodiment of a positioning member 130 that may be used to assist coupling and orienting the distal end 58 of the handpiece 50 to the tooth 10 so that the high-velocity jet 60 is directed through the inlet opening 84 in the side of the tooth 10. In the illustrated embodiment, the positioning member 130 comprises a collar portion 134 that may be generally disk-like in shape. The collar portion 134 may have a width in a range from about 1 mm to about 10 mm. The collar portion 134 may have a substantially central opening 136 having a diameter approximately equal to the diameter of the inlet opening 84. In some embodiments, the collar portion 134 is formed from a flexible material (such as an elastomer) so that it can conform to the surface of the tooth 10. An adhesive (such as a light-cured orthodontic adhesive) may be included on a surface 134a of the collar portion 134 to enable the positioning member 130 to adhere to the tooth 10. In some embodiments, a detachable, elongated peg 138 may be used to position the position member 130 so that the central opening 136 in the collar portion 134 is aligned with the inlet opening 84 in the tooth 10. A distal end of the peg 138 may be sized to fit within the opening 84. When the positioning member 130 is in position on the tooth 10 and the adhesive has sufficiently cured, the peg 138 may be removed, leaving the positioning member 130 adhered to the side of the tooth 10 (see FIG. 6D). Additionally or alternatively, the collar portion 134 may include alignment guides disposed near the opening 136 to assist positioning the member 130 over the opening 84. For example, a circular ridge, having an outside diameter slightly smaller than the inside diameter of the opening 84, may be formed on the surface 134a around the opening 136 and used to align the openings 84 and 136.

The positioning member 130 may include mounting portions 132a configured to engage complementary mounting portions 132b disposed on the distal end 58 of the handpiece 50. For example, the mounting portions 132a, 132b may comprise a standard, quick-turn connector such as a Luer-lock. FIG. 6D schematically illustrates the handpiece 50 before (or after) engagement with the positioning member 130. When engaged with the positioning member 130, the handpiece 50 advantageously is oriented so that the jet axis 70 is substantially longitudinally aligned with the inlet opening 84. Moreover, the positioning member 130 may stabilize the handpiece 50 against unwanted movement. Accordingly, upon actuation, the jet 60 will be directed through the opening 84 and into the pulp cavity 26. As further described below with reference to FIG. 10B, the distal end 58 of the handpiece 50 may comprise one or more pressure sensors adapted to sense when the distal end 58 is securely engaged with the positioning member 130. In such embodiments, the system may not permit the jet 60 to be actuated until a sufficiently secure fit and proper alignment are indicated by signals from the pressure sensors.

When the distal end 58 of the handpiece 50 is engaged with the positioning member 130, the jet 60 may be directed through the inlet opening 84 so that it impacts the dentinal wall and causes detachment of the organic material in the root canal spaces 30. After the treatment is completed, the positioning member 130 may be removed from the tooth 10 using any well-known technique for releasing the adhesive. Remaining adhesive, if present, may function as bonding for restorative material used to close the defect.

To reduce possible buildup of fluid pressure within the pulp cavity 26, a relief opening 88 may be formed in the top side (e.g., occlusal surface) of the tooth 10. The relief opening 88 may be formed on a buccal or lingual surface. The diameter of the relief outlet or opening 88 may be larger than that of the inlet opening 84, for example, about 2 mm to about 3 mm. In some methods, the diameter of the relief opening 88 may be about the same as (or smaller than) the diameter of the inlet opening 84 (e.g., about 1.2 mm in one embodiment). The relief opening 88 also serves to facilitate debridement and evacuation of the detached organic material. The diameter of the relief opening 88 advantageously may be large enough to permit flushing out pulp fragments. In some methods, two or more relief openings 88 may be used.

Those skilled in dentistry will recognize that the inlet and relief openings 84, 88 are quite small relative to the openings required for conventional root canal procedures, thus preserving valuable tooth structure. For example, in some methods, even though two openings 84, 88 are used, less tooth material is removed than in a conventional root canal procedure using a single, standard-sized occlusal opening. Moreover, many patients have existing coronal defects (e.g., decay, restorations, preparations, etc.), and it may be possible to form one or both of the openings simply by removing material other than healthy tooth tissue, such as a filling. Fillings on one or more sides of the tooth 10 may also be used to form the openings 84, 88. In any event, once the jet has caused acoustically induced detachment of the organic material, low pressure flushing fluid (such as water) may be introduced into either or both the openings 84, 88 to irrigate the canal space 30 and flush out the organic material. Additionally and optionally, manual extraction of organic material may be performed with a dental instrument.

Certain teeth, particularly molars and/or wisdom teeth, may be difficult to access in conventional root canal therapies due to limited working space in the back of the mouth. Due to the difficulties or inconvenience of coronal access to these teeth in conventional root canal therapies, some of these teeth, which would otherwise be treatable, may instead be extracted. An advantage of some embodiments of the disclosed methods is that by permitting a wider range of access with the liquid jet 60 (e.g., on or through coronal, lingual, and/or buccal surfaces), the acoustic-induced detachment of organic material can save the tooth and reduce the likelihood of its extraction.

Without subscribing to any particular theory of operation, FIG. 7 schematically illustrates an explanation for the effectiveness of the treatment methods described herein. FIG. 7 depicts the jet 60 impacting the dentin 20 of the tooth 10. Upon impact, a portion of the energy and/or momentum carried by the jet 60 generates an acoustic pressure wave 100 that propagates through the body of the tooth 10. In addition to propagating through the dentin 20, the acoustic wave 100 may propagate through organic material in the root canal space 30 and in the tubules of the dentin 20. The acoustic wave 100 may include acoustic energy with acoustic frequencies in a range from about 1 Hz to above 5 MHz such as, for example, up to about 10 MHz. The acoustic wave 100 may have frequency components in the ultrasonic frequency range, e.g., above about 20 kHz. In some cases, the frequency range may include megasonic frequencies above about 1 MHz. The acoustic wave 100 may include other frequencies as well.

At the dentinal surfaces of the root canal space 30 and tubules, the acoustic wave 100 may cause surrounding liquid to cavitate. This cavitation may be a surface effect cavitation caused by conversion of the water (or other liquid) from a liquid state to a vapor state. If the acoustic energy in the wave 100 is sufficiently large, the cavitation processes may include inertial cavitation wherein sufficiently low pressures caused by the acoustic wave 100 induce formation and collapse of bubbles in liquid near the dentinal surfaces. For smaller acoustic energies, non-inertial (or gas) cavitation may play a more significant role. In such cases, dissolved gases, tissue debris, and impurities act as nucleation centers for the formation of cavitation bubbles. Cavitation may also occur at pore sites across the microporous surface of the dentin 20. The cavitation bubbles oscillate in response to the acoustic wave 100, and amplitude of the oscillations may grow as additional gas is absorbed by the bubble.

Due to the relatively high energy required for formation of cavitation bubbles, collapse of the cavitation bubble occurs with great force against the surface of the dentin 20. Bubble collapse near a surface is known to occur asymmetrically and may result in formation of cavitation jets that radiate toward the surface and produce locally very high pressures and/or elevated temperatures. In some cases, the acoustic wave 100 may also generate fluid motions (acoustic streaming) that enhance disruption of organic matter. Acoustic streaming also may be effective at transporting or flushing detached organic matter out of the root canal space 30 and/or the tubules.

Accordingly, in certain methods, the acoustic wave 100 cleans the root canal system through processes including formation and collapse of cavitation bubbles, radiation of cavitation jets toward dentinal surfaces, acoustic streaming, or a combination thereof. In the process, the organic material may be broken into small pieces or particles, which can be irrigated from the pulp cavity 26. In some treatment methods, these cavitation processes may produce transient, localized high pressure and/or elevated temperature zones that disrupt, detach, and/or delaminate organic matter near root canal surfaces. For example, cavitation-induced effects may detach odontoblasts from the dentinal surface and effectively remove a portion of the odontoblastic process from the tubule. Cavitation-induced effects may also disrupt and/or detach the collagen fibrils that attach the odontoblast layer to the pulp in the interior of the canal space 30. Cavitation-induced effects may also occur in interior regions of the pulp cavity 26 (e.g., away from the dentinal surfaces) and may disrupt and/or loosen organic material in the interior regions, thereby making this material more readily removable from the pulp cavity 26.

Cavitation effects are believed to be formed everywhere the acoustic wave 100 propagates with sufficient energy. Accordingly, it is advantageous for the jet 60 to have sufficient energy and/or momentum to generate an acoustic wave 100 capable of causing cavitation effects throughout substantially the entire root canal system but without causing harm to the tooth 10. For example, if the jet diameter D is too small and the momentum of the jet beam too high, impact of the beam may cause significant dentinal erosion. On the other hand, if the beam diameter D is too large and the momentum of the jet beam too low, the beam may have insufficient energy to produce an acoustic pressure wave 100 capable of causing cavitation. For example, in certain methods, the jet energy incident on the tooth is greater than about 20 J to provide effective cleaning but less than about 400 J to prevent dentinal erosion. In some methods, acoustic cavitation effects occur substantially throughout the root canal system when certain jet 60 properties are above threshold values. For example, in one experiment mentioned above, widespread acoustic noise (possibly caused by acoustic cavitation) was detected in a tooth only when the energy flux of the jet 60 was greater than about 75 kW/cm$^2$. At the onset of detectable acoustic noise, the jet had a power of about 2 W, a velocity of about 115 m/s, a mass flow rate of about 0.3 g/s, and provided a force of about 0.03 N. The efficiency of conversion of jet kinetic energy into acoustic energy was estimated to be about 2%.

A portion of the acoustic wave 100 may also propagate through tissue and bone adjacent the tooth 10. However, the energy carried by this portion of the acoustic wave 100 may be relatively small due to the acoustic impedance mismatch between the dentin 20 and nearby tissues and bone. Accordingly, cavitation-induced effects may be substantially reduced in tissues surrounding the tooth 10, and the endodontic methods described herein will not significantly damage the surrounding tissues.

Figure 8A:
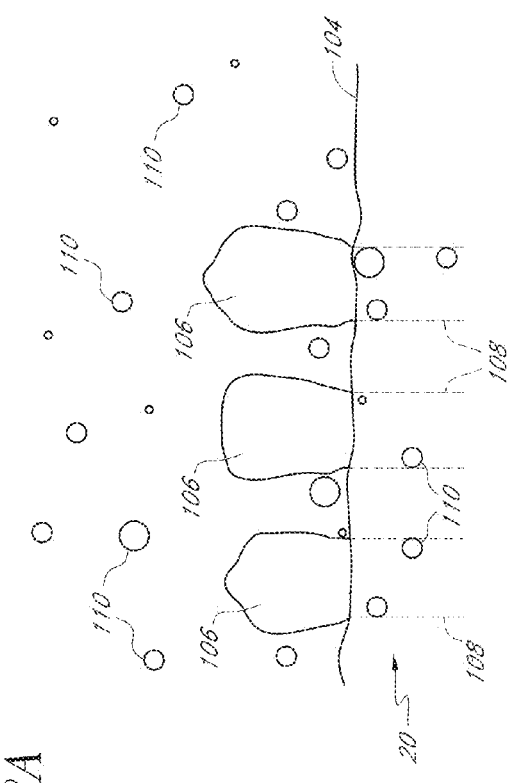
FIG. 8A is a cross-section view schematically illustrating cavitation bubbles formed near odontoblasts at the dentinal surface.
Figure 8B:
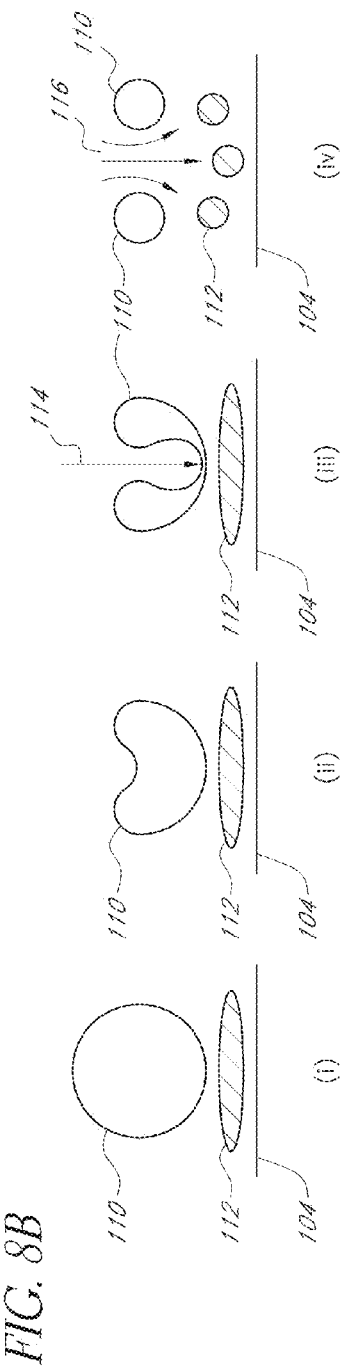
FIG. 8B schematically illustrates collapse of a cavitation bubble and formation of a cavitation jet near a dentinal surface.

FIGS. 8A and 8B are cross-section views that schematically illustrate some of the cavitation processes that clean a surface 104 of the dentin 20. As depicted in FIG. 8A, odontoblasts 106 are located near the surface and the odontoblastic process extends into the tubules 108. The acoustic wave 100 induces oscillation and collapse of cavitation bubbles 110, which generates transient localized heat and/or pressure that disrupts and detaches the odontoblasts 106 from the dentinal surface 104. Cavitation bubbles may also form and collapse within the tubules 108, thereby causing disruption of the odontoblastic processes in the tubules 108. FIG. 8B schematically depicts collapse of an initially spherical cavitation bubble 110 (shown in (i)) located near the body of organic matter 112 adjacent the dentinal surface 104 and filling the canal. In (ii), the side of the bubble 110 away from the surface 104 is perturbed from its spherical shape. In (iii), fluid 114 from the interior of the pulp cavity 26 penetrates the perturbed side of the bubble 110. In (iv) the fluid 114 has formed a cavitation jet 116 radiating toward the surface 104. The energy and momentum of the cavitation jet 116 breaks up and disperses the organic matter 112.

Figure 9A:
FIGS. 9A-9C are scanning electron microscope photographs of dentinal surfaces following treatment of the tooth with the high-velocity jet.
Figure 9B:
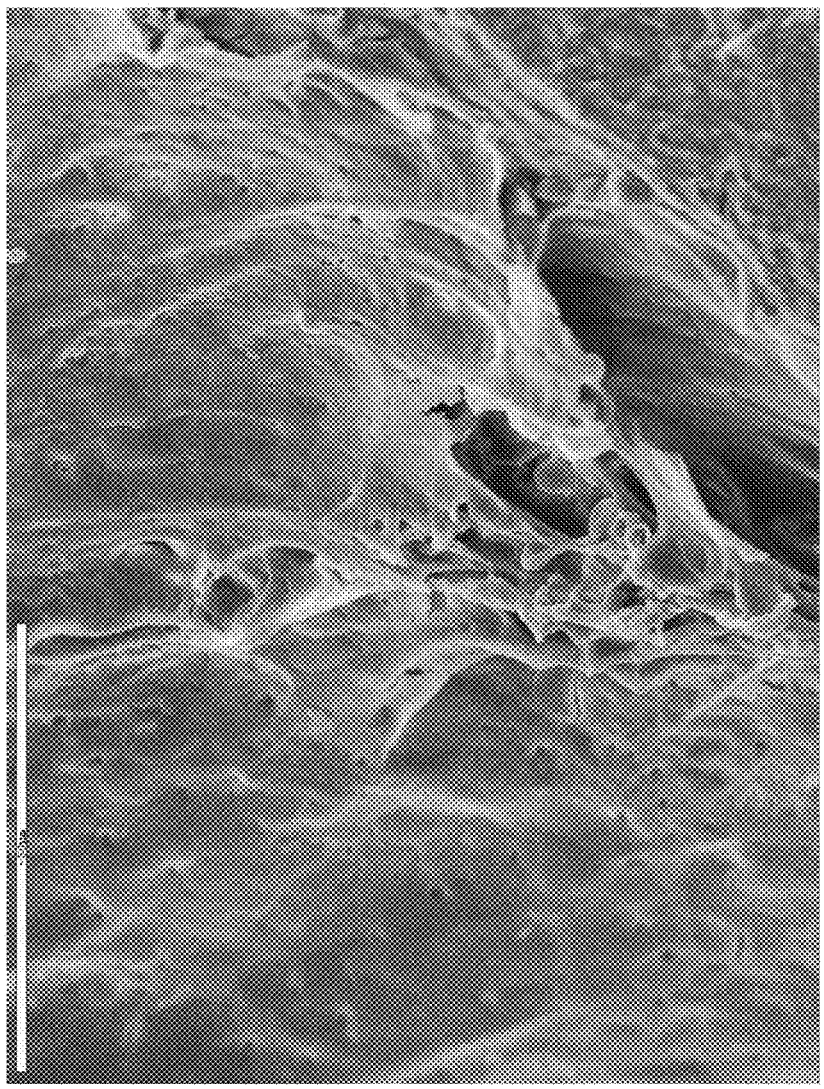
Figure 9C:
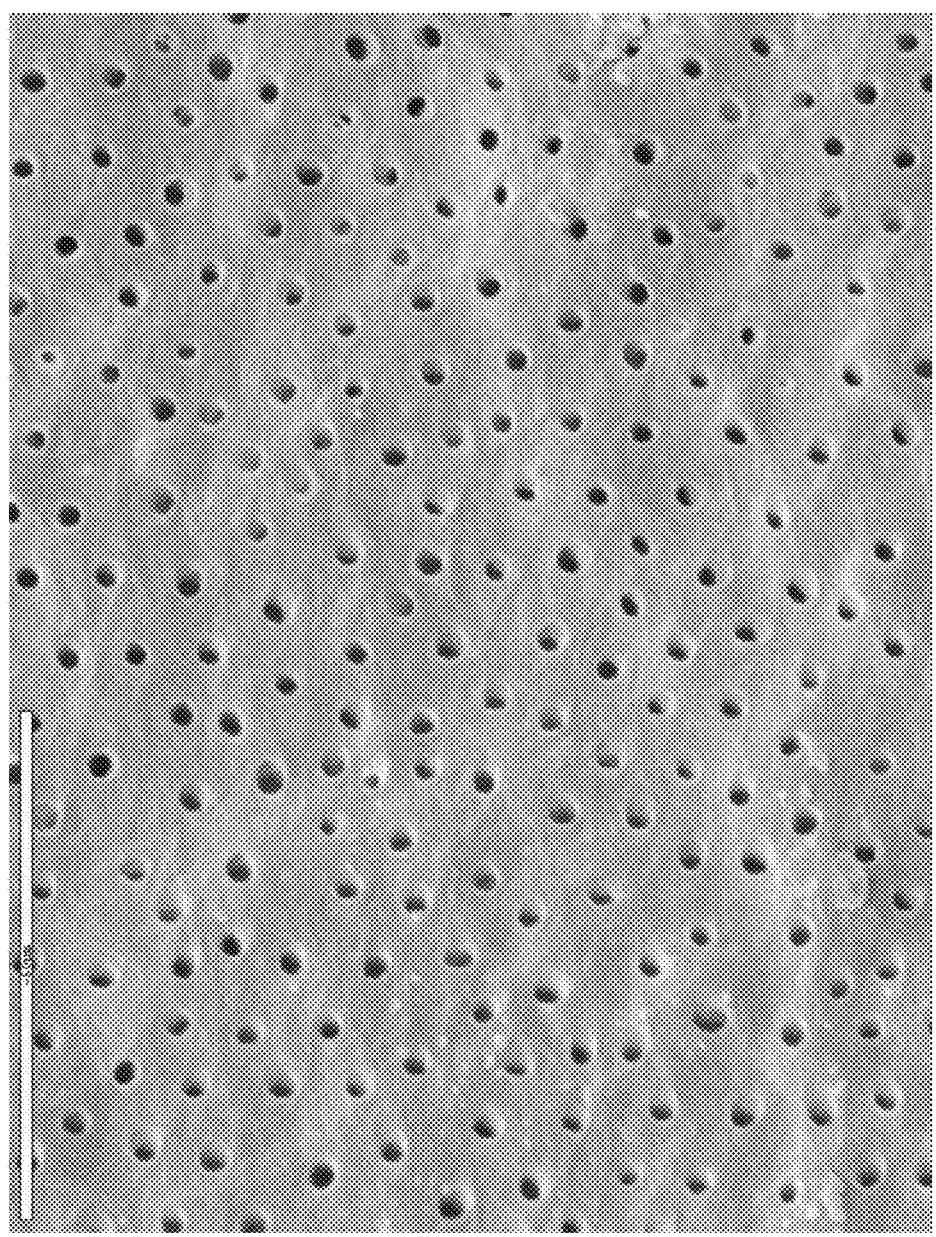

FIGS. 9A-9C are scanning electron microscope photographs of the dentinal surface showing the surprising effectiveness of the removal of organic matter by the acoustic effect. FIG. 9A shows dentinal tubules in an apical area of a mature tooth magnified 1000×. FIGS. 9B and 9C show dentin and dentinal tubules magnified 1000× in an inclusion area of a juvenile tooth (FIG. 9B) and in a medial area of a mature root (FIG. 9C). A bar at the top left of each photo indicates the linear scale (in microns) for each photograph. As can be seen in FIGS. 9A-9C, the dentinal surfaces are almost entirely free from organic matter, which appears to have been literally ripped away from the dentin. Flow of liquid in the root canal space 30 flushes and irrigates the organic matter from substantially all the root canal space 30 and the tubules. Returning to FIG. 2, this photograph shows an apical area of a mature tooth magnified 2000× and viewed at a slight slant from perpendicular to show that the tubules have been cleaned down to a distance of about 3 microns. FIGS. 2 and 9A-9C demonstrate that cleaning of the dentinal surface is very effective and that almost no remnants of organic material remain after treatment.

As mentioned previously, it has been found that the cleaning does not require that the liquid jet 60 be aimed down the root canal space 30, although that may be beneficial in certain isolated cases where the canal space 30 is very narrow and/or filled with dry material. Additionally, it has been found in some embodiments that the pulp cavity 26 need not be prepared or pre-treated (e.g., by removing root canal matter with one or more endodontic files) before application of the jet. Impingement of the jet 60 onto the dentin 20 in the pulp chamber 28 is sufficient in most cases to generate the acoustic wave 100 that causes the cleaning. Accordingly, in most cases, it is the acoustic wave 100 and not direct impact of the jet 60 that causes the cleaning, particularly for the dentinal surfaces near the apex of the root canal space 30, which are remote from the pulp chamber 28. For example, examination of FIGS. 2 and 9A-9C shows that organic material has been removed from apical dentinal tubules, which are not possible to reach directly with the liquid jet beam. In certain embodiments, the jet beam 60 is capable of delivering sufficient energy to the tooth 10 to remove at least 90 percent of the organic material from the root canal system. In other embodiments, at least 95 percent of the organic material is removed. Preferably, the jet beam should be capable of removing substantially all the organic material from the root canal space 30 and from at least a portion of the tubules. The treatment time during which the high-velocity jet is directed toward the tooth 10 may range from about 1 second to about 120 seconds. In some embodiments, the treatment time is from about 10 seconds to about 30 seconds. In other embodiments, the treatment time is no more than 10 seconds such as, for example, less than about 5 seconds, less than about 2 seconds, less than about 1 second, less than about 0.5 second, or less than about 0.1 second.

The high-velocity jet 60 may produce significant mechanical power (e.g., tens of Watts in some embodiments). When the jet 60 is directed toward the tooth 10, a fraction of this mechanical power may go toward heating the tooth 10 as well as nearby teeth and gums. To avoid discomfort to the patient, in some embodiments, excess heat, if present, may be removed by, for example, irrigating the tooth under treatment with a stream of liquid (e.g., water at room temperature or cooler). The stream of liquid can absorb and carry away some or all of the excess heat, if present, that may be produced by the jet 60. The stream of liquid may be aspirated from the patient's mouth.

The methods described herein may be used as standalone treatments for root canal procedures, or they may be used in conjunction with other dental treatments (which may or may not involve liquid jet methods).

The high-velocity jet treatment methods described herein may be particularly effective in certain system operating ranges. For example, a jet having an energy flux greater than about 75 kW/cm$^2$ may be particularly effective.

The apparatus and methods described above may include additional devices and components configured to provide additional functionality to the endodontic treatment system. FIGS. 10A-10H schematically illustrate embodiments of a contact member configured as a cap 120 that may be attached to and detached from the distal end 58 of the handpiece 50. In some embodiments, the cap 120 may have threads that engage complimentary threads on the distal end 58 of the handpiece 50 (see, e.g., FIG. 10B). The cap 120 can be fitted around the crown 12 of the tooth 10 and used to orient the jet 60 toward a suitable opening into the pulp chamber 26. The cap 120 may be used to orient the distal end 58 of the handpiece 50 so that the liquid jet 60 is directed obliquely at a dentinal surface on the floor 82 (and/or sides) of the pulp cavity 26 and not directly down any of the canal space 30. The cap 120 may be formed from a transparent or translucent material and may be sufficiently flexible to fit around teeth having a range of sizes. In some embodiments, the distal end 58 of the handpiece 50 may be rotatable and/or extendable with respect to the cap 120 so that the jet 60 may be moved closer to or further from a desired tooth portion. The cap 120 may include an outflow opening to permit organic material and liquid to be evacuated from the tooth 10. Alternatively, the cap may include a suction port so that fluid may be removed from the pulp chamber at substantially the same volume as it is introduced. The suction port thus prevents any of the removed diseased tissue and liquid from entering the patient's mouth. Another aspect of the invention comprises introducing a volume of liquid in the form of a jet into a pulp chamber of a tooth and removing a volume of liquid from the pulp chamber at substantially the same rate that it is introduced. Preferably, removal is accomplished by suction. In certain embodiments, the distal end 58 of the handpiece 50 may include multiple orifices which provide multiple jets, and the cap 120 may be used to orient the handpiece 50 such that jets are directed not only at the floor 82 (and/or sides) of the pulp chamber 28, but also towards entrances to the canal spaces 30. In some embodiments, the handpiece 50 may also be tilted and rotated to allow the jet 60 to be aimed axially into all canal openings.

As schematically shown in FIGS. 10C-10H, a plurality of caps 120 may be configured to fit over teeth of different sizes and shapes. Advantageously, each different cap 120 may be color coded to permit easy selection by the dentist during a treatment procedure. The cap 120 may also be sized and shaped to fit within an opening formed in the tooth 10 at the beginning of certain endodontic procedures (such as the openings 80, 84, and 88; see FIGS. 6A-6C), rather than fitting over or around the exterior of the tooth 10.

Figure 10A:
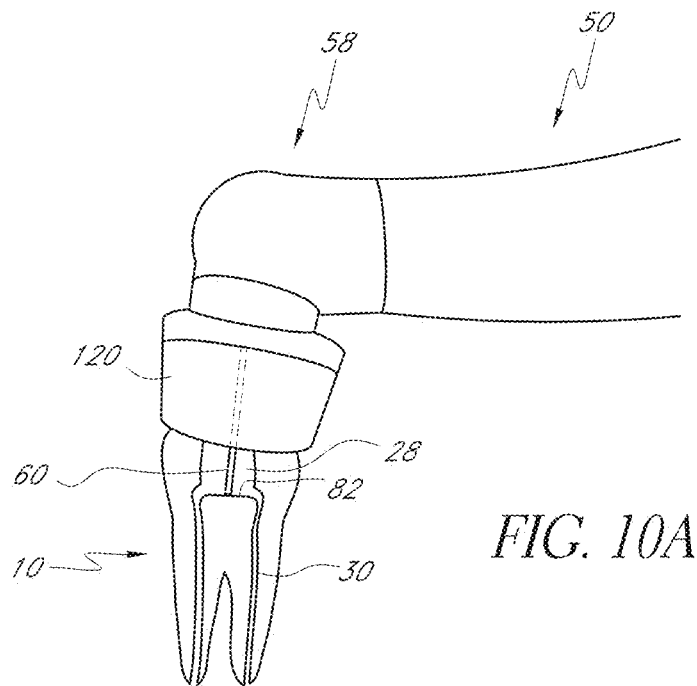
FIGS. 10A-10H schematically illustrate embodiments of a cap that may be attached to a distal end of a handpiece and fitted onto a tooth.
Figure 10B:
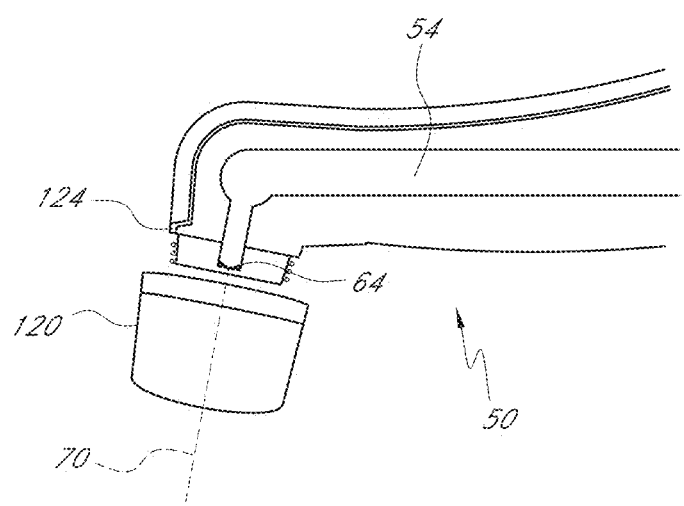
Figure 10D:
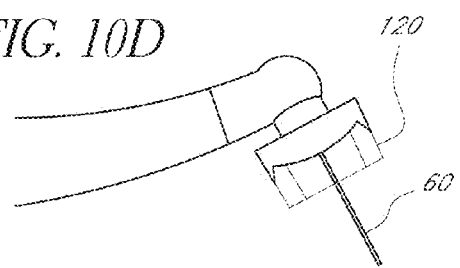
Figure 10E:
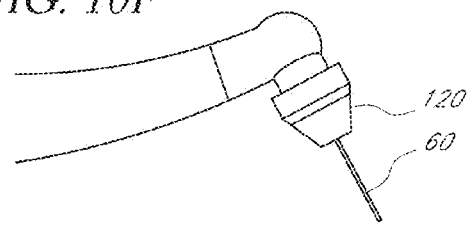
Figure 10F:
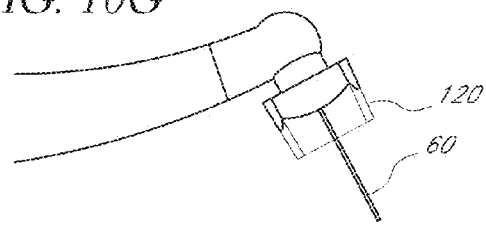
Figure 10G:
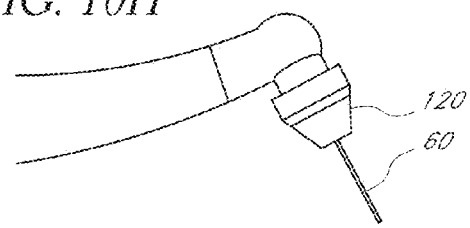
Figure 10H:
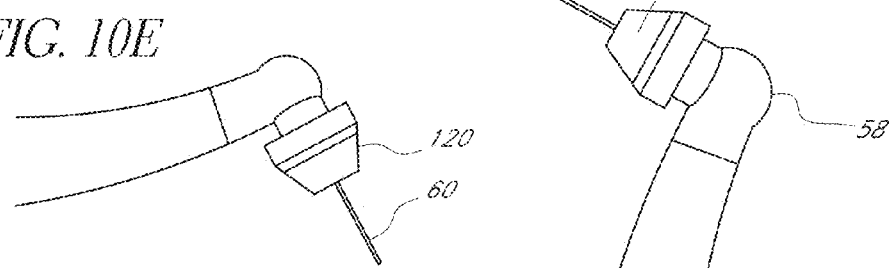
Figure 10C:
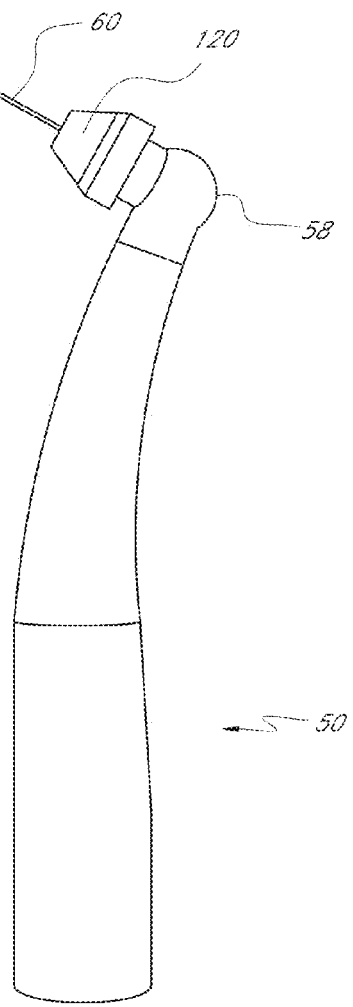

As depicted in the partially exploded cross-section view shown in FIG. 10B, the distal end 58 of the handpiece 50 may include one or more pressure sensors 124. As the cap 120 is urged onto a tooth (or into an opening in the tooth), the pressure sensor 124 provides a signal that indicates when a sufficiently "tight" fit has been achieved. The pressure sensor 124 may be electrically connected to the controller 52, and enables the jet 60 to operate only when the sensor senses contact. A suitable audible, visible, and/or tactile signal may be output (e.g., by the user interface 54 or by an output device on the handpiece 50) to indicate that the cap 120 is in position on the tooth 10.

The system may also include a distance sensor to indicate the distance between the distal end 58 of the handpiece 50 and a surface of the tooth 10. The distance sensor may provide an audible, tactile, and/or visible indication when the distal end 58 is at a suitable distance from the surface for operation of the liquid jet 60 (e.g., not too close to damage the tooth and not too far for the jet to be ineffective). In one embodiment, the distance sensor comprises a pair of optical elements mounted on the handpiece and spaced from each other. Each optical element directs an optical beam that intersects the other beam a predetermined distance away from the handpiece 50. The operator of the handpiece 50 can maneuver the handpiece 50 until the intersecting beams illuminate a desired portion of the tooth 10 and then actuate the liquid jet 60. The optical elements may comprise light-emitting diodes (LEDs) and/or lasers. In some embodiments, more than two optical elements may be used (e.g., to indicate a range of distances).

A person of ordinary skill will recognize that a wide variety of sensors may be used in addition to or instead of the pressure sensor 124 and/or the distance sensor. For example, certain embodiments utilize one or more electric, magnetic, acoustic, and/or optical sensors to determine position and/or orientation of the handpiece 50 (or portions thereof) in the mouth. For example, proximity sensors, including capacitive sensors, ultrasonic sensors, light reflectance sensors, magnetic inductance sensors, and so forth, may be used. Certain embodiments may comprise one or more orientation sensors (e.g., accelerometers) configured to sense the orientation of the longitudinal jet axis 70 relative to one or more reference landmarks in the mouth (e.g., a portion of the tooth 10 such as the openings 80, 84, 88). The system may include a timer configured to deactuate the jet 60 after a predetermined time interval to reduce likelihood of damage to the tooth 10 and/or root canal system. Systems comprising one or more such sensors advantageously may provide increased safety. For example, certain such embodiments may prevent (or inhibit) an operator from actuating the liquid jet 60 until the distal end 58 of the handpiece 50 is suitably positioned and/or oriented adjacent the tooth 10.

Figure 11:
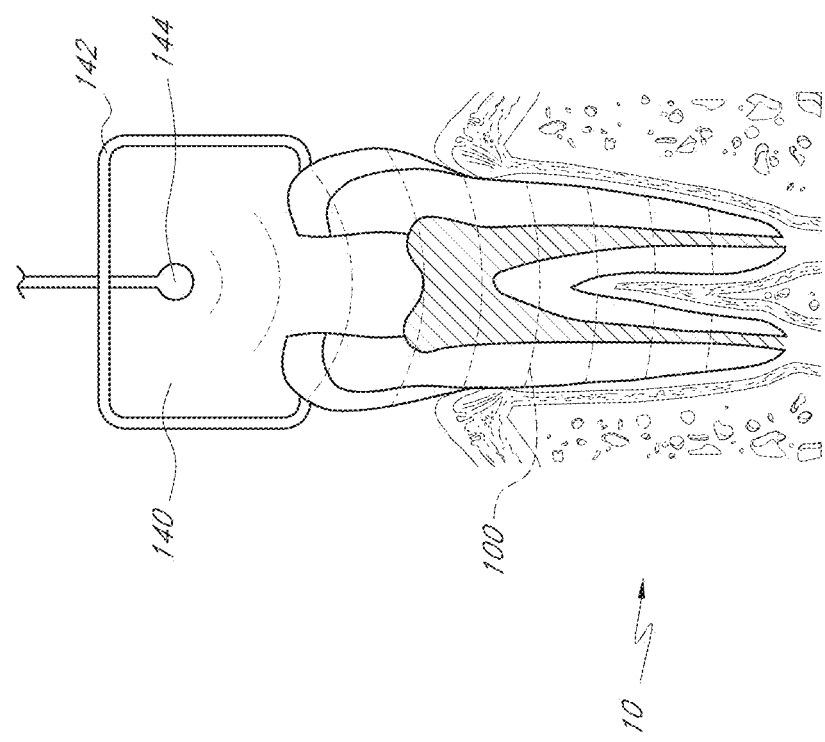
FIG. 11 schematically illustrates a method for generating an acoustic wave using a piezoelectric transducer.

As described herein, acoustic energy capable of producing cavitation may be particularly effective at cleaning the root canal system. It has been found that this acoustic energy may be efficiently produced by directing a high-velocity beam of liquid onto a portion of the tooth. However, the scope of the present disclosure is not limited to methods using high-velocity jets. In other embodiments, the acoustic energy is generated by vibrating mechanical devices (e.g., a piezoelectric transducer), ultrasonic (or megasonic) generators (e.g., an ultrasonic and/or a megasonic horn), or any other component capable of producing acoustic vibrations. FIG. 11 schematically illustrates one method for generating the acoustic wave 100 using a piezoelectric transducer 144. In this method, an enclosure 142 is attached to the tooth 10. The enclosure 142 comprises a chamber 140 filled with a liquid (e.g., water). The transducer 144 is disposed in or on the chamber 140. When actuated, the transducer 144 vibrates, which causes the acoustic wave 100 to propagate through the surrounding fluid and the tooth 10. The acoustic wave 100 cleans the root canal system substantially as described above. Because the vibrating transducer 144 is not in direct contact with the tooth 10, possible damage to the tooth 10 is reduced or eliminated. Although in FIG. 11 a mechanical transducer 144 is used to generate the acoustic wave 100, in other embodiments, the acoustic wave 100 may be produced by, for example, directing the high-velocity liquid jet into or onto the enclosure 142. In such embodiments, the enclosure 142 acts as an "acoustic waveguide" converting jet kinetic energy into acoustic energy that propagates through the tooth 10 as the acoustic wave 100. Beneficially, the liquid in the chamber 140 may absorb excess mechanical energy which may otherwise produce unwanted heat in the tooth 10. In another embodiment, an ultrasonic horn is disposed near the enclosure 142 and used to generate the acoustic wave 100.

Any of the procedures described herein may be carried out with the use of a rubber dam. Further although the tooth 10 depicted in the figures is a molar, one of ordinary skill in the art will appreciate that the procedures may be performed on any type of tooth such as an incisor, a canine, a bicuspid, or a molar. Also, the disclosed methods are capable of cleaning root canal spaces having a wide range of morphologies, including highly curved root canal spaces which are difficult to clean using conventional dental techniques. Moreover, the disclosed methods may be performed on human teeth (including children's teeth) and/or on animal teeth.

The foregoing description sets forth various preferred embodiments and other illustrative but non-limiting embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method/process may be performed in any suitable sequence and are not necessarily limited to any particular disclosed sequence.

Accordingly, the scope of the inventions disclosed herein is to be determined according to the following claims and their equivalents.

What is claimed is:

1. A method for treating an infected or decaying condition in a tooth, the method comprising:
providing a liquid medium at a treatment region of the tooth including the infected or decaying condition, wherein providing a liquid medium at the treatment region comprises supplying a substantially degassed liquid;
generating a pulsed coherent energy beam with a pressure wave generator;
directing the pulsed coherent energy beam into the liquid medium present at the treatment region of the tooth; and
generating pressure waves within the liquid medium to remove infected or decaying material from the tooth at the treatment region.

2. The method of claim 1, further comprising
generating pressure waves of sufficient energy to remove infected or decaying material from the tooth throughout the treatment region, including at locations remote from the portion of the treatment region at which the pulsed coherent energy beam is directed.

3. The method of claim 1, additionally comprising directing the pulsed coherent energy beam against a surface in the tooth.

4. The method of claim 1, additionally comprising generating pressure waves of sufficient energy to create surface-effect cavitation at an infected or decaying surface of the tooth.

5. The method of claim 1, wherein generating a pulsed coherent energy beam comprises activating a liquid jet device to produce a collimated, coherent liquid jet and varying the liquid pressure within the liquid jet device.

6. The method of claim 5 additionally comprising activating a pump to pressurize the liquid that forms the liquid jet.

7. The method of claim 6, wherein a pressure of the liquid that forms the liquid jet is in a range from about 2,000 psi to about 11,000 psi.

8. The method of claim 1, wherein the generated pressure waves comprise frequencies within a widespread range of acoustic noise.

9. The method of claim 8, wherein the frequencies comprise frequencies in a range from about 1 Hz to about 10 MHz.

10. The method of claim 1, wherein the pulsed coherent energy beam has a pulse frequency in a range from about 0.1 Hz to about 10 MHz.

11. The method of claim 1, additionally comprising removing organic material from a root canal of the tooth without directing the coherent energy beam down the root canal.

12. The method of claim 11, wherein removing organic material comprises removing substantially all organic material from lateral canal branches.

13. The method of claim 1, additionally comprising applying a cap to the tooth, the cap disposed about the pressure wave generator.

14. The method of claim 1, additionally comprising removing fluid from the treatment region through a suction port.

15. A method for treating an infected or decaying condition in a tooth, the method comprising:

supplying fluid to a treatment region of the tooth including the infected or decaying condition in the tooth wherein supplying fluid comprises supplying a substantially degassed liquid; and directing a coherent energy beam into the supplied fluid to generate pressure waves through the fluid, the generated pressure waves being sufficient to treat the infected or decaying condition.

16. The method of claim 15, further comprising directing the coherent energy beam into the supplied fluid at a portion of the treatment region to generate pressure waves through the fluid, the generated pressure waves having sufficient energy to remove infected or decaying material throughout the treatment region, including at locations remote from the portion of the treatment region at which the coherent energy beam is directed.

17. The method of claim 15, additionally comprising generating a pulsed coherent energy beam.

18. The method of claim 15, additionally comprising generating pressure waves of sufficient energy to create surface-effect cavitation at an infected or decaying surface of the tooth.

19. The method of claim 15, further comprising directing the coherent energy beam against a surface in the tooth.

20. The method of claim 15 additionally comprising avoiding directing the coherent energy beam down a root canal of the tooth while directing the coherent energy beam into the supplied fluid.

\* \* \* \* \*

UNITED STATES PATENT AND TRADEMARK OFFICE
CERTIFICATE OF CORRECTION

PATENT NO. : 10,016,263 B2  
APPLICATION NO. : 15/217843  
DATED : July 10, 2018  
INVENTOR(S) : Gharib et al.

Page 1 of 1

It is certified that error appears in the above-identified patent and that said Letters Patent is hereby corrected as shown below:

On the Title Page

Item (74) for Attorney, Agent, or Firm, Line 1, please correct the "Matens" to -- Martens --.

On page 7, Item (56), Column 1, Line 37, under Other Publications, please change "ala" to -- a la --.

In the Claims

In Claim 20, Column 21, Line 25, please change "claim 15" to -- claim 15, --.

Signed and Sealed this  
Twenty-fifth Day of December, 2018

Andrei Iancu  
*Director of the United States Patent and Trademark Office*